(12) United States Patent
Bann et al.

(10) Patent No.: US 10,188,716 B2
(45) Date of Patent: Jan. 29, 2019

(54) PROTECTIVE ANTIGEN COMPLEXES WITH INCREASED STABILITY AND USES THEREOF

(71) Applicants: Wichita State University, Wichita, KS (US); Case Western Reserve University, Cleveland, OH (US)

(72) Inventors: James G. Bann, Wichita, KS (US); Masaru Miyagi, Cleveland, OH (US)

(73) Assignees: Wichita State University, Wichita, KS (US); Case Western Reserve University, Cleveland, OH (US)

( * ) Notice: Subject to any disclaimer, the term of this patent is extended or adjusted under 35 U.S.C. 154(b) by 0 days.

(21) Appl. No.: 15/886,112

(22) Filed: Feb. 1, 2018

(65) Prior Publication Data

US 2018/0169208 A1     Jun. 21, 2018

Related U.S. Application Data

(62) Division of application No. 14/987,505, filed on Jan. 4, 2016.

(60) Provisional application No. 62/099,356, filed on Jan. 2, 2015.

(51) Int. Cl.
| | | |
|---|---|---|
| *A61K 39/002* | (2006.01) | |
| *A61K 39/07* | (2006.01) | |
| *A61K 39/40* | (2006.01) | |
| *A61K 45/06* | (2006.01) | |
| *A61K 39/00* | (2006.01) | |

(52) U.S. Cl.
CPC .............. *A61K 39/07* (2013.01); *A61K 39/40* (2013.01); *A61K 45/06* (2013.01); *A61K 2039/6031* (2013.01); *A61K 2039/622* (2013.01)

(58) Field of Classification Search
None
See application file for complete search history.

(56) References Cited

U.S. PATENT DOCUMENTS 7,731,979 B2    6/2010   Bann

OTHER PUBLICATIONS

Rajapaksha et al (Protein Science. 2012. 21:1467-1480).*
Mullangi et al (Biochemistry. 2014. 53: 6084-6091).*
Williams et al (Protein Science. 2009. 18: 2277-2286).*
Chadegani, Fatemeh, et al., F Nuclear Magnetic Resonance and Crystallographic Studies of 5-Fluorotryptophan-Labeled Anthrax Protective Antigen and Effects of the Receptor on Stability, Copyright 2014 American Chemical Society, Open Access on Jan. 3, 2015, Biochemistry 2014, 53, 690-701 (12 pages).
Wimalasena, D. Shyamili et al, Evidence That Histidine Protonation of Receptor-Bound Anthrax Protective Antigen is a Trigger for Pore Formation, Biochemistry, 2010, 49 (33), pp. 6973-6983, DOI: 10.1021/bi100647z, Publication Date (Web): Jul. 22, 2010, Copyright © 2010 American Chemical Society (11 pages).
Rajapaksha, Maheshinie et al., pH effects on binding between the anthrax protective antigen and the host cellular receptor CMG2, Protein Science: A Publication of the Protein Society. 2012;21(10):1467-1480. doi:10.1002/pro.2136 (14 pages).
Williams, Alexander S et al., Domain 4 of the anthrax protective antigen maintains structure and binding to the host receptor CMG2 at low pH, Protein Science 2009, 18: 2277-2286. doi:10.1002/pro. 238, Aug. 31, 2009 (10 pages).
Hu, Lei et al., Comparison of the Structural Stability and Dynamic Properties of Recombinant Anthrax Protective Antigen and Its 2-Fluorohistidine-Labeled Analogue, Journal of Pharmaceutical Sciences, vol. 101, No. 11, Nov. 2012, doi: 10.1002/jps.23294. Epub Aug. 21, 2012 (11 pages).
Mullangi, Vennela et al, Long-Range Stabilization of Anthrax Protective Antigen upon Binding to CMG2, Biochemistry, 2014, 53 (38), pp. 6084-6091, DOI: 10.1021/bi500718g, Publication Date (Web): Sep. 3, 2014 Copyright © 2014 American Chemical Society (8 pages).
Zhang, Jeney et al., Stabilization of vaccines and antibiotics in silk and eliminating the cold chain, Proc Natl Acad Sci U S A. Jul. 24, 2012; 109(30): 11981-11986. Published online Jul. 9, 2012. doi: 10.1073/pnas.1206210109 PMCID: PMC3409735 (6 pages).
Office Action in corresponding U.S. Appl. No. 14/987,505, dated Nov. 8, 2017.

* cited by examiner

*Primary Examiner* — Jennifer E Graser
(74) *Attorney, Agent, or Firm* — Hovey Williams LLP

(57) ABSTRACT

Immunogenic compositions against *Bacillus anthracis* comprising a stabilized protective antigen complex are disclosed. The stabilized complex comprises protective antigen protein and capillary morphogenesis protein-2, with the capillary morphogenesis protein-2 being bound to the protective antigen protein along a binding interface. The stabilized protective antigen complex has increased thermal and structural stability, along with resistance to premature proteolytic degradation. Methods of using the same to induce an immunogenic response in a subject against *B. anthracis* infection are also disclosed.

19 Claims, 11 Drawing Sheets
(3 of 11 Drawing Sheet(s) Filed in Color)
Specification includes a Sequence Listing.

SEQUENCE LISTING

```
<160> NUMBER OF SEQ ID NOS: 9

<210> SEQ ID NO 1
<211> LENGTH: 764
<212> TYPE: PRT
<213> ORGANISM: Bacillus anthracis

<400> SEQUENCE: 1

Met Lys Lys Arg Lys Val Leu Ile Pro Leu Met Ala Leu Ser Thr Ile
1               5                   10                  15

Leu Val Ser Ser Thr Gly Asn Leu Glu Val Ile Gln Ala Glu Val Lys
            20                  25                  30

Gln Glu Asn Arg Leu Leu Asn Glu Ser Glu Ser Ser Ser Gln Gly Leu
        35                  40                  45

Leu Gly Tyr Tyr Phe Ser Asp Leu Asn Phe Gln Ala Pro Met Val Val
    50                  55                  60

Thr Ser Ser Thr Thr Gly Asp Leu Ser Ile Pro Ser Ser Glu Leu Glu
65                  70                  75                  80

Asn Ile Pro Ser Glu Asn Gln Tyr Phe Gln Ser Ala Ile Trp Ser Gly
                85                  90                  95

Phe Ile Lys Val Lys Lys Ser Asp Glu Tyr Thr Phe Ala Thr Ser Ala
            100                 105                 110

Asp Asn His Val Thr Met Trp Val Asp Asp Gln Glu Val Ile Asn Lys
        115                 120                 125

Ala Ser Asn Ser Asn Lys Ile Arg Leu Glu Lys Gly Arg Leu Tyr Gln
    130                 135                 140

Ile Lys Ile Gln Tyr Gln Arg Glu Asn Pro Thr Glu Lys Gly Leu Asp
145                 150                 155                 160

Phe Lys Leu Tyr Trp Thr Asp Ser Gln Asn Lys Lys Glu Val Ile Ser
                165                 170                 175
```

-continued

```
Ser Asp Asn Leu Gln Leu Pro Glu Leu Lys Gln Lys Ser Asn Ser
            180                 185                 190

Arg Lys Lys Arg Ser Thr Ser Ala Gly Pro Thr Val Pro Asp Arg Asp
            195                 200                 205

Asn Asp Gly Ile Pro Asp Ser Leu Glu Val Glu Gly Tyr Thr Val Asp
            210                 215                 220

Val Lys Asn Lys Arg Thr Phe Leu Ser Pro Trp Ile Ser Asn Ile His
225                 230                 235                 240

Glu Lys Lys Gly Leu Thr Lys Tyr Lys Ser Ser Pro Glu Lys Trp Ser
                245                 250                 255

Thr Ala Ser Asp Pro Tyr Ser Asp Phe Glu Lys Val Thr Gly Arg Ile
            260                 265                 270

Asp Lys Asn Val Ser Pro Glu Ala Arg His Pro Leu Val Ala Ala Tyr
            275                 280                 285

Pro Ile Val His Val Asp Met Glu Asn Ile Ile Leu Ser Lys Asn Glu
            290                 295                 300

Asp Gln Ser Thr Gln Asn Thr Asp Ser Gln Thr Arg Thr Ile Ser Lys
305                 310                 315                 320

Asn Thr Ser Thr Ser Arg Thr His Thr Ser Glu Val His Gly Asn Ala
                325                 330                 335

Glu Val His Ala Ser Phe Phe Asp Ile Gly Gly Ser Val Ser Ala Gly
            340                 345                 350

Phe Ser Asn Ser Asn Ser Ser Thr Val Ala Ile Asp His Ser Leu Ser
            355                 360                 365

Leu Ala Gly Glu Arg Thr Trp Ala Glu Thr Met Gly Leu Asn Thr Ala
            370                 375                 380

Asp Thr Ala Arg Leu Asn Ala Asn Ile Arg Tyr Val Asn Thr Gly Thr
385                 390                 395                 400

Ala Pro Ile Tyr Asn Val Leu Pro Thr Thr Ser Leu Val Leu Gly Lys
                405                 410                 415

Asn Gln Thr Leu Ala Thr Ile Lys Ala Lys Glu Asn Gln Leu Ser Gln
            420                 425                 430

Ile Leu Ala Pro Asn Asn Tyr Tyr Pro Ser Lys Asn Leu Ala Pro Ile
            435                 440                 445

Ala Leu Asn Ala Gln Asp Asp Phe Ser Ser Thr Pro Ile Thr Met Asn
450                 455                 460

Tyr Asn Gln Phe Leu Glu Leu Glu Lys Thr Lys Gln Leu Arg Leu Asp
465                 470                 475                 480

Thr Asp Gln Val Tyr Gly Asn Ile Ala Thr Tyr Asn Phe Glu Asn Gly
                485                 490                 495

Arg Val Arg Val Asp Thr Gly Ser Asn Trp Ser Glu Val Leu Pro Gln
            500                 505                 510

Ile Gln Glu Thr Thr Ala Arg Ile Ile Phe Asn Gly Lys Asp Leu Asn
            515                 520                 525

Leu Val Glu Arg Arg Ile Ala Ala Val Asn Pro Ser Asp Pro Leu Glu
            530                 535                 540

Thr Thr Lys Pro Asp Met Thr Leu Lys Glu Ala Leu Lys Ile Ala Phe
545                 550                 555                 560

Gly Phe Asn Glu Pro Asn Gly Asn Leu Gln Tyr Gln Gly Lys Asp Ile
                565                 570                 575

Thr Glu Phe Asp Phe Asn Phe Asp Gln Gln Thr Ser Gln Asn Ile Lys
            580                 585                 590
```

```
Asn Gln Leu Ala Glu Leu Asn Ala Thr Asn Ile Tyr Thr Val Leu Asp
        595                 600                 605
Lys Ile Lys Leu Asn Ala Lys Met Asn Ile Leu Ile Arg Asp Lys Arg
610                 615                 620
Phe His Tyr Asp Arg Asn Asn Ile Ala Val Gly Ala Asp Glu Ser Val
625                 630                 635                 640
Val Lys Glu Ala His Arg Glu Val Ile Asn Ser Ser Thr Glu Gly Leu
                645                 650                 655
Leu Leu Asn Ile Asp Lys Asp Ile Arg Lys Ile Leu Ser Gly Tyr Ile
                660                 665                 670
Val Glu Ile Glu Asp Thr Glu Gly Leu Lys Glu Val Ile Asn Asp Arg
            675                 680                 685
Tyr Asp Met Leu Asn Ile Ser Ser Leu Arg Gln Asp Gly Lys Thr Phe
        690                 695                 700
Ile Asp Phe Lys Lys Tyr Asn Asp Lys Leu Pro Leu Tyr Ile Ser Asn
705                 710                 715                 720
Pro Asn Tyr Lys Val Asn Val Tyr Ala Val Thr Lys Glu Asn Thr Ile
                725                 730                 735
Ile Asn Pro Ser Glu Asn Gly Asp Thr Ser Thr Asn Gly Ile Lys Lys
                740                 745                 750
Ile Leu Ile Phe Ser Lys Lys Gly Tyr Glu Ile Gly
            755                 760
```

<210> SEQ ID NO 2
<211> LENGTH: 2369
<212> TYPE: DNA
<213> ORGANISM: Bacillus anthracis

<400> SEQUENCE: 2

```
aatttcaata taatataaat ttaattttat acaaaaagga gaacgtatat gaaaaaacga      60
aaagtgttaa taccattaat ggcattgtct acgatattag tttcaagcac aggtaattta     120
gaggtgattc aggcagaagt taaacaggag aaccggttat taaatgaatc agaatcaagt     180
tcccaggggt tactaggata ctatttagt gatttgaatt ttcaagcacc catggtggtt     240
acctcttcta ctacagggga tttatctatt cctagttctg agttagaaaa tattccatcg     300
gaaaaccaat attttcaatc tgctatttgg tcaggattta tcaaagttaa gagagtgat      360
gaatatacat ttgctacttc cgctgataat catgtaacaa tgtgggtaga tgaccaagaa     420
gtgattaata agcttctaa ttctaacaaa atcagattag aaaaaggaag attatatcaa     480
ataaaaattc aatatcaacg agaaaatcct actgaaaaag gattggattt caagttgtac     540
tggaccgatt ctcaaaataa aaaagaagtg atttctagtg ataacttaca attgccagaa     600
ttaaaacaaa atcttcgaa ctcaagaaaa aagcgaagta caagtgctgg acctacggtt     660
ccagaccgtg acaatgatgg aatccctgat tcattagagg tagaaggata tacggttgat     720
gtcaaaaata aagaactttt tcttttcacca tggatttcta atattcatga aaagaaagga     780
ttaaccaaat ataaatcatc tcctgaaaaa tggagcacgg cttctgatcc gtacagtgat     840
ttcgaaaagg ttacaggacg gattgataag aatgtatcac cagaggcaag acacccctt      900
gtggcagctt atccgattgt acatgtagat atggagaata ttattctctc aaaaaatgag     960
gatcaatcca cacagaatac tgatagtcaa acgagaacaa taagtaaaaa tacttctaca    1020
agtaggacac atactagtga agtacatgga aatgcagaag tgcatgcgtc gttcttgat     1080
attggtggga gtgtatctgc aggatttagt aattcgaatt caagtacggt cgcaattgat    1140
```

-continued

```
cattcactat ctctagcagg ggaaagaact tgggctgaaa caatgggttt aaataccgct    1200
gatacagcaa gattaaatgc caatattaga tatgtaaata ctgggacggc tccaatctac    1260
aacgtgttac caacgacttc gttagtgtta ggaaaaaatc aaacactcgc gacaattaaa    1320
gctaaggaaa accaattaag tcaaatactt gcacctaata attattatcc ttctaaaaac    1380
ttggcgccaa tcgcattaaa tgcacaagac gatttcagtt ctactccaat acaatgaat     1440 tacaatcaat ttcttgagtt agaaaaaacg aaacaattaa gattagatac ggatcaagta    1500
tatgggaata tagcaacata caattttgaa aatggaagag tgagggtgga tacaggctcg    1560
aactggagtg aagtgttacc gcaaattcaa gaaacaactg cacgtatcat ttttaatgga    1620
aaagatttaa atctggtaga aaggcggata gcggcggtta tcctagtga tccattagaa     1680 acgactaaac cggatatgac attaaaagaa gcccttaaaa tagcatttgg atttaacgaa    1740
ccgaatggaa acttacaata tcaagggaaa gacataaccg aatttgattt taatttcgat    1800
caacaaacat ctcaaaatat caagaatcag ttagcggaat taaacgcaac taacatatat    1860
actgtattag ataaaatcaa attaaatgca aaaatgaata ttttaataag agataaacgt    1920
tttcattatg atagaaataa catagcagtt ggggcggatg agtcagtagt taaggaggct    1980
catagagaag taattaattc gtcaacagag ggattattgt taaatattga aggatata     2040 agaaaaatat tatcaggtta tattgtagaa attgaagata ctgaagggct taagaagtt    2100 ataaatgaca gatatgatat gttgaatatt tctagtttac ggcaagatgg aaaaacattt    2160
atagatttta aaaatataa tgataaatta ccgttatata aagtaatcc caattataag      2220 gtaaatgtat atgctgttac taaagaaaac actattatta atcctagtga gaatggggat    2280
actagtacca acgggatcaa gaaaatttta atcttttcta aaaaaggcta tgagatagga    2340
taaggtaatt ctaggtgatt tttaaatta                                       2369
```

<210> SEQ ID NO 3
<211> LENGTH: 764
<212> TYPE: PRT
<213> ORGANISM: Bacillus anthracis

<400> SEQUENCE: 3

```
Met Lys Lys Arg Lys Val Leu Ile Pro Leu Met Ala Leu Ser Thr Ile
1               5                   10                  15

Leu Val Ser Ser Thr Gly Asn Leu Glu Val Ile Gln Ala Glu Val Lys
            20                  25                  30

Gln Glu Asn Arg Leu Leu Asn Glu Ser Glu Ser Ser Gln Gly Leu
        35                  40                  45

Leu Gly Tyr Tyr Phe Ser Asp Leu Asn Phe Gln Ala Pro Met Val Val
    50                  55                  60

Thr Ser Ser Thr Thr Gly Asp Leu Ser Ile Pro Ser Ser Glu Leu Glu
65                  70                  75                  80

Asn Ile Pro Ser Glu Asn Gln Tyr Phe Gln Ser Ala Ile Trp Ser Gly
                85                  90                  95

Phe Ile Lys Val Lys Lys Ser Asp Glu Tyr Thr Phe Ala Thr Ser Ala
            100                 105                 110

Asp Asn His Val Thr Met Trp Val Asp Asp Gln Glu Val Ile Asn Lys
        115                 120                 125

Ala Ser Asn Ser Asn Lys Ile Arg Leu Glu Lys Gly Arg Leu Tyr Gln
    130                 135                 140

Ile Lys Ile Gln Tyr Gln Arg Glu Asn Pro Thr Glu Lys Gly Leu Asp
145                 150                 155                 160
```

```
Phe Lys Leu Tyr Trp Thr Asp Ser Gln Asn Lys Lys Glu Val Ile Ser
            165                 170                 175

Ser Asp Asn Leu Gln Leu Pro Glu Leu Lys Gln Lys Ser Ser Asn Ser
        180                 185                 190

Arg Lys Lys Arg Ser Thr Ser Ala Gly Pro Thr Val Pro Asp Arg Asp
            195                 200                 205

Asn Asp Gly Ile Pro Asp Ser Leu Glu Val Glu Gly Tyr Thr Val Asp
        210                 215                 220

Val Lys Asn Lys Arg Thr Phe Leu Ser Pro Trp Ile Ser Asn Ile His
225                 230                 235                 240

Glu Lys Lys Gly Leu Thr Lys Tyr Lys Ser Ser Pro Glu Lys Trp Ser
                245                 250                 255

Thr Ala Ser Asp Pro Tyr Ser Asp Phe Glu Lys Val Thr Gly Arg Ile
            260                 265                 270

Asp Lys Asn Val Ser Pro Glu Ala Arg His Pro Leu Val Ala Ala Tyr
        275                 280                 285

Pro Ile Val His Val Asp Met Glu Asn Ile Ile Leu Ser Lys Asn Glu
        290                 295                 300

Asp Gln Ser Thr Gln Asn Thr Asp Ser Gln Thr Arg Thr Ile Ser Lys
305                 310                 315                 320

Asn Thr Ser Thr Ser Arg Thr His Thr Ser Glu Val His Gly Asn Ala
                325                 330                 335

Glu Val His Ala Ser Phe Phe Asp Ile Gly Gly Ser Val Ser Ala Gly
            340                 345                 350

Phe Ser Asn Ser Asn Ser Ser Thr Val Ala Ile Asp His Ser Leu Ser
        355                 360                 365

Leu Ala Gly Glu Arg Thr Trp Ala Glu Thr Met Gly Leu Asn Thr Ala
        370                 375                 380

Asp Thr Ala Arg Leu Asn Ala Asn Ile Arg Tyr Val Asn Thr Gly Thr
385                 390                 395                 400

Ala Pro Ile Tyr Asn Val Leu Pro Thr Thr Ser Leu Val Leu Gly Lys
            405                 410                 415

Asn Gln Thr Leu Ala Thr Ile Lys Ala Lys Glu Asn Gln Leu Ser Gln
        420                 425                 430

Ile Leu Ala Pro Asn Asn Tyr Tyr Pro Ser Lys Asn Leu Ala Pro Ile
        435                 440                 445

Ala Leu Asn Ala Gln Asp Asp Phe Ser Ser Thr Pro Ile Thr Met Asn
        450                 455                 460

Tyr Asn Gln Phe Leu Glu Leu Glu Lys Thr Lys Gln Leu Arg Leu Asp
465                 470                 475                 480

Thr Asp Gln Val Tyr Gly Asn Ile Ala Thr Tyr Asn Phe Glu Asn Gly
            485                 490                 495

Arg Val Arg Val Asp Thr Gly Ser Asn Trp Ser Glu Val Leu Pro Gln
            500                 505                 510

Ile Gln Glu Thr Thr Ala Arg Ile Ile Phe Asn Gly Lys Asp Leu Asn
        515                 520                 525

Leu Val Glu Arg Arg Ile Ala Ala Val Asn Pro Ser Asp Pro Leu Glu
        530                 535                 540

Thr Thr Lys Pro Asp Met Thr Leu Lys Glu Ala Leu Lys Ile Ala Phe
545                 550                 555                 560

Gly Phe Asn Glu Pro Asn Gly Asn Leu Gln Tyr Gln Gly Lys Asp Ile
            565                 570                 575
```

```
Thr Glu Phe Asp Phe Asn Phe Asp Gln Gln Thr Ser Gln Asn Ile Lys
                580                 585                 590

Asn Gln Leu Ala Glu Leu Asn Ala Thr Asn Ile Tyr Thr Val Leu Asp
            595                 600                 605

Lys Ile Lys Leu Asn Ala Lys Met Asn Ile Leu Ile Arg Asp Lys Arg
        610                 615                 620

Phe His Tyr Asp Arg Asn Asn Ile Ala Val Gly Ala Asp Glu Ser Val
625                 630                 635                 640

Val Lys Glu Ala His Arg Glu Val Ile Asn Ser Ser Thr Glu Gly Leu
                645                 650                 655

Leu Leu Asn Ile Asp Lys Asp Ile Arg Lys Ile Leu Ser Gly Tyr Ile
            660                 665                 670

Val Glu Ile Glu Asp Thr Glu Gly Leu Lys Glu Val Ile Asn Asp Arg
        675                 680                 685

Tyr Asp Met Leu Asn Ile Ser Ser Leu Arg Gln Asp Gly Lys Thr Phe
690                 695                 700

Ile Asp Phe Lys Lys Tyr Asn Asp Lys Leu Pro Leu Tyr Ile Ser Asn
705                 710                 715                 720

Pro Asn Tyr Lys Val Asn Val Tyr Ala Val Thr Lys Glu Asn Thr Ile
                725                 730                 735

Ile Asn Pro Ser Glu Asn Gly Asp Thr Ser Thr Asn Gly Ile Lys Lys
            740                 745                 750

Ile Leu Ile Phe Ser Lys Lys Gly Tyr Glu Ile Gly
        755                 760

<210> SEQ ID NO 4
<211> LENGTH: 489
<212> TYPE: PRT
<213> ORGANISM: Homo sapiens

<400> SEQUENCE: 4

Met Val Ala Glu Arg Ser Pro Ala Arg Ser Pro Gly Ser Trp Leu Phe
1               5                   10                  15

Pro Gly Leu Trp Leu Leu Val Leu Ser Gly Pro Gly Gly Leu Leu Arg
            20                  25                  30

Ala Gln Glu Gln Pro Ser Cys Arg Arg Ala Phe Asp Leu Tyr Phe Val
        35                  40                  45

Leu Asp Lys Ser Gly Ser Val Ala Asn Asn Trp Ile Glu Ile Tyr Asn
    50                  55                  60

Phe Val Gln Gln Leu Ala Glu Arg Phe Val Ser Pro Glu Met Arg Leu
65                  70                  75                  80

Ser Phe Ile Val Phe Ser Ser Gln Ala Thr Ile Ile Leu Pro Leu Thr
                85                  90                  95

Gly Asp Arg Gly Lys Ile Ser Lys Gly Leu Glu Asp Leu Lys Arg Val
            100                 105                 110

Ser Pro Val Gly Glu Thr Tyr Ile His Glu Gly Leu Lys Leu Ala Asn
        115                 120                 125

Glu Gln Ile Gln Lys Ala Gly Gly Leu Lys Thr Ser Ser Ile Ile Ile
    130                 135                 140

Ala Leu Thr Asp Gly Lys Leu Asp Gly Leu Val Pro Ser Tyr Ala Glu
145                 150                 155                 160

Lys Glu Ala Lys Ile Ser Arg Ser Leu Gly Ala Ser Val Tyr Cys Val
                165                 170                 175

Gly Val Leu Asp Phe Glu Gln Ala Gln Leu Glu Arg Ile Ala Asp Ser
            180                 185                 190
```

```
Lys Glu Gln Val Phe Pro Val Lys Gly Gly Phe Gln Ala Leu Lys Gly
            195                 200                 205
Ile Ile Asn Ser Ile Leu Ala Gln Ser Cys Thr Glu Ile Leu Glu Leu
        210                 215                 220
Gln Pro Ser Ser Val Cys Val Gly Glu Glu Phe Gln Ile Val Leu Ser
225                 230                 235                 240
Gly Arg Gly Phe Met Leu Gly Ser Arg Asn Gly Ser Val Leu Cys Thr
                245                 250                 255
Tyr Thr Val Asn Glu Thr Tyr Thr Thr Ser Val Lys Pro Val Ser Val
                260                 265                 270
Gln Leu Asn Ser Met Leu Cys Pro Ala Pro Ile Leu Asn Lys Ala Gly
            275                 280                 285
Glu Thr Leu Asp Val Ser Val Ser Phe Asn Gly Gly Lys Ser Val Ile
        290                 295                 300
Ser Gly Ser Leu Ile Val Thr Ala Thr Glu Cys Ser Asn Gly Ile Ala
305                 310                 315                 320
Ala Ile Ile Val Ile Leu Val Leu Leu Leu Leu Gly Ile Gly Leu
                325                 330                 335
Met Trp Trp Phe Trp Pro Leu Cys Cys Lys Val Val Ile Lys Asp Pro
                340                 345                 350
Pro Pro Pro Pro Ala Pro Ala Pro Lys Glu Glu Glu Glu Pro Leu
                355                 360                 365
Pro Thr Lys Lys Trp Pro Thr Val Asp Ala Ser Tyr Tyr Gly Gly Arg
        370                 375                 380
Gly Val Gly Gly Ile Lys Arg Met Glu Val Arg Trp Gly Asp Lys Gly
385                 390                 395                 400
Ser Thr Glu Glu Gly Ala Arg Leu Glu Lys Ala Lys Asn Ala Val Val
                405                 410                 415
Lys Ile Pro Glu Glu Thr Glu Glu Pro Ile Arg Pro Arg Pro Pro Arg
                420                 425                 430
Pro Lys Pro Thr His Gln Pro Gln Thr Lys Trp Tyr Thr Pro Ile
        435                 440                 445
Lys Gly Arg Leu Asp Ala Leu Trp Ala Leu Leu Arg Arg Gln Tyr Asp
        450                 455                 460
Arg Val Ser Leu Met Arg Pro Gln Glu Gly Asp Glu Val Cys Ile Trp
465                 470                 475                 480
Glu Cys Ile Glu Lys Glu Leu Thr Ala
                485

<210> SEQ ID NO 5
<211> LENGTH: 406
<212> TYPE: PRT
<213> ORGANISM: Homo sapiens

<400> SEQUENCE: 5

Met Ser Pro Ile Leu Gly Tyr Trp Lys Ile Lys Gly Leu Val Gln Pro
1               5                   10                  15
Thr Arg Leu Leu Leu Glu Tyr Leu Glu Glu Lys Tyr Glu Glu His Leu
            20                  25                  30
Tyr Glu Arg Asp Glu Gly Asp Lys Trp Arg Asn Lys Lys Phe Glu Leu
        35                  40                  45
Gly Leu Glu Phe Pro Asn Leu Pro Tyr Tyr Ile Asp Gly Asp Val Lys
    50                  55                  60
```

```
Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
210                 215                 220

Gly Ser Cys Arg Arg Ala Phe Asp Leu Tyr Phe Val Leu Asp Lys Ser
225                 230                 235                 240

Gly Ser Val Ala Asn Asn Trp Ile Glu Ile Tyr Asn Phe Val Gln Gln
                245                 250                 255

Leu Ala Glu Arg Phe Val Ser Pro Glu Met Arg Leu Ser Phe Ile Val
            260                 265                 270

Phe Ser Ser Gln Ala Thr Ile Ile Leu Pro Leu Thr Gly Asp Arg Gly
        275                 280                 285

Lys Ile Ser Lys Gly Leu Glu Asp Leu Lys Arg Val Ser Pro Val Gly
290                 295                 300

Glu Thr Tyr Ile His Glu Gly Leu Lys Leu Ala Asn Glu Gln Ile Gln
305                 310                 315                 320

Lys Ala Gly Gly Leu Lys Thr Ser Ser Ile Ile Ala Leu Thr Asp
                325                 330                 335

Gly Lys Leu Asp Gly Leu Val Pro Ser Tyr Ala Glu Lys Glu Ala Lys
            340                 345                 350

Ile Ser Arg Ser Leu Gly Ala Ser Val Tyr Cys Val Gly Val Leu Asp
        355                 360                 365

Phe Glu Gln Ala Gln Leu Glu Arg Ile Ala Asp Ser Lys Glu Gln Val
370                 375                 380

Phe Pro Val Lys Gly Gly Phe Gln Ala Leu Lys Gly Ile Ile Asn Ser
385                 390                 395                 400

Ile Leu Ala Gln Ser Cys
                405

<210> SEQ ID NO 6
<211> LENGTH: 67
<212> TYPE: DNA
<213> ORGANISM: Bacillus anthracis

<400> SEQUENCE: 6
cggttgatgt caaaaataaa agaactttc tttcaccata catttctaat attcatgaaa    60
agaaagg                                                              67
```

```
<210> SEQ ID NO 7
<211> LENGTH: 46
<212> TYPE: DNA
<213> ORGANISM: Bacillus anthracis

<400> SEQUENCE: 7
tctcctgaaa aattcagcac ggcttctgat ccgtacagtg atttcg            46

<210> SEQ ID NO 8
<211> LENGTH: 47
<212> TYPE: DNA
<213> ORGANISM: Bacillus anthracis

<400> SEQUENCE: 8
cattcactat ctctagcagg ggaaagaact tacgctgaaa caatggg           47

<210> SEQ ID NO 9
<211> LENGTH: 45
<212> TYPE: DNA
<213> ORGANISM: Bacillus anthracis

<400> SEQUENCE: 9
gagtgagggt ggatacaggc tcgaacttta gtgaagtgtt accgc             45
```

PROTECTIVE ANTIGEN COMPLEXES WITH INCREASED STABILITY AND USES THEREOF

CROSS-REFERENCE TO RELATED APPLICATIONS

The present application is a divisional of U.S. Ser. No. 14/987,505, filed Jan. 4, 2016, which claims the priority benefit of U.S. Provisional Patent Application Ser. No. 62/099,356, filed Jan. 2, 2015, entitled PROTECTIVE ANTIGEN COMPLEXES WITH INCREASED STABILITY AND USES THEREOF, each of which is incorporated by reference in its entirety herein.

FEDERALLY SPONSORED RESEARCH OR DEVELOPMENT

The present invention was supported in part by the National Institutes of Health ("NIH") grant R21-EY021595, and NIH-KINBRE award under INBRE Grant P20GM10341, and the federal government may have certain rights in the invention.

SEQUENCE LISTING

The following application contains a sequence listing in computer readable format (CRF), submitted as a text file in ASCII format entitled "SequenceListing," created on Jan. 4, 2016, as 25 KB. The content of the CRF is hereby incorporated by reference.

BACKGROUND OF THE INVENTION

Field of the Invention

The present invention relates to stabilized protective antigen complexes and compositions, methods, and kits related to the same.

Description of Related Art

Protein subunit vaccines tend to be unstable and readily undergo physical and/or chemical degradation. There is a need for stabilized vaccines not only for storage during distribution, but for the preservation of native structures that are critical to inducing protective immunity.

The etiologic agent of anthrax (*Bacillus anthracis*) is a potential threat as an agent of biowarfare or bioterrorism because exposure to aerosolized *B. anthracis* spores can be lethal to mammals, such as humans. Anthrax toxin is a member of the class of bacterial toxins termed A-B toxins. A-B toxins are composed of two moieties. The A moiety is the enzymic portion of the toxin that catalyzes the toxic effect upon a cytoplasmic target within a target cell. The B moiety binds to a cellular receptor and facilitates the translocation of the A moiety across the cell membrane into the cytoplasm of the cell.

The B moieties of A-B toxins from tetanus, botulinum, diphtheria, and anthrax all form channels in membranes. The A and B moieties of anthrax toxin are secreted from the bacterial cell as distinct polypeptides. The A and B subunits of other A-B toxins are produced as single chain polypeptides or as separate chains that are assembled into oligomeric toxins before release from the bacteria.

The A-B toxin secreted from *Bacillus anthracis* is comprised of the B moiety protective antigen ("PA"), and the A moieties edema factor ("EF"), and lethal factor ("LF"). EF is a calmodulin-dependent adenylate cyclase which may protect the bacteria from destruction by phagocytes. LF is a metalloprotease that can kill macrophages or, at lower concentrations, prevent macrophages from secreting cytokines, resulting in a compromised host immunity. PA is a channel forming polypeptide that allows entry of EF and LF across membranes into the cell, a step that is critical for the pathogenesis of anthrax. PA is secreted as a four-domain, 83 kD protein that recognizes on the host cells the von-Willebrand factor A domain ("VWA") of two integrin-like receptors: anthrax toxin receptor 1, ("ANTXR1", formerly anthrax toxin receptor-tumor endothelial marker 8), and anthrax toxin receptor 2 ("ANTXR2", formerly capillary morphogenesis protein 2 ("CMG2")). Binding of PA to the receptor results in the proteolytic cleavage of PA by a furin-like protease on the cell surface, releasing the first 167 amino acid residues of domain 1. Thus, the C-terminal 63 kDa fragment ("$PA_{63}$") remains bound to the cell and the N-terminal 20 kDa fragment ("$PA_{20}$") dissociates from $PA_{63}$. This proteolytic cleavage and subsequent dissociation of $PA_{20}$ confer at least two new properties on $PA_{63}$: (1) the ability to oligomerize into a ring-shaped heptameric sodium dodecyl sulfate ("SDS")-dissociable structure termed prepore and (2) the ability to bind EF and LF, which bind with a stoichiometry of three per heptameric prepore. Binding of PA to the receptor also initiates receptor-mediated endocytosis into an endosomal compartment, which eventually becomes acidified. The low pH within the endosome induces a conformational change in the protective antigen that results in the formation of a membrane spanning channel, and this new conformation of the entire PA heptamer is termed the pore. The pore allows the transport of EF and LF into the cytosol. The exact pH required for pore formation is dependent upon interactions with the receptor—in vitro studies indicate that the pH is about 5 if the receptor is ANTXR2, and a slightly higher pH (about 6) if the receptor is ANTXR1. The receptor then dissociates from PA, allowing conformational changes to occur throughout the protein such that PA forms a membrane spanning pore. Modified forms of PA have been developed for use as vaccine and antitoxins, including those described in U.S. Pat. No. 7,731,979, incorporated by reference herein in its entirety. However, storage and stability of such proteins remains a significant challenge.

SUMMARY OF THE INVENTION

The present invention is broadly concerned with immunogenic compositions against *Bacillus anthracis* infection comprising a stabilized protective antigen complex. The stabilized complex comprises protective antigen protein and capillary morphogenesis protein-2. The capillary morphogenesis protein-2 is bound to protective antigen protein along a binding interface which increases the thermal and/or structural stability of the protective antigen, and imparts resistance to degradation.

Methods for inducing an immunogenic response in a subject against *B. anthracis* are also disclosed. The methods generally comprising administering to the subject a therapeutically-effective amount of an immunogenic composition according to the various embodiments of the invention.

Kits for vaccinating a subject against *B. anthracis* infection are also disclosed. The kits generally comprise a unit dosage form of an immunogenic composition according to the various embodiments of the invention and instructions for administering the unit dosage form to the subject.

Also described herein are methods for stabilizing protective antigen for a vaccine or antitoxin against *B. anthracis*. The methods generally comprise providing an immunogenic composition against *B. anthracis* infection, which comprises protective antigen, and adding purified capillary morphogenesis protein-2 to the composition. Advantageously, the resulting composition has increased thermal stability, and does not require a cold chain for storage and transportation.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
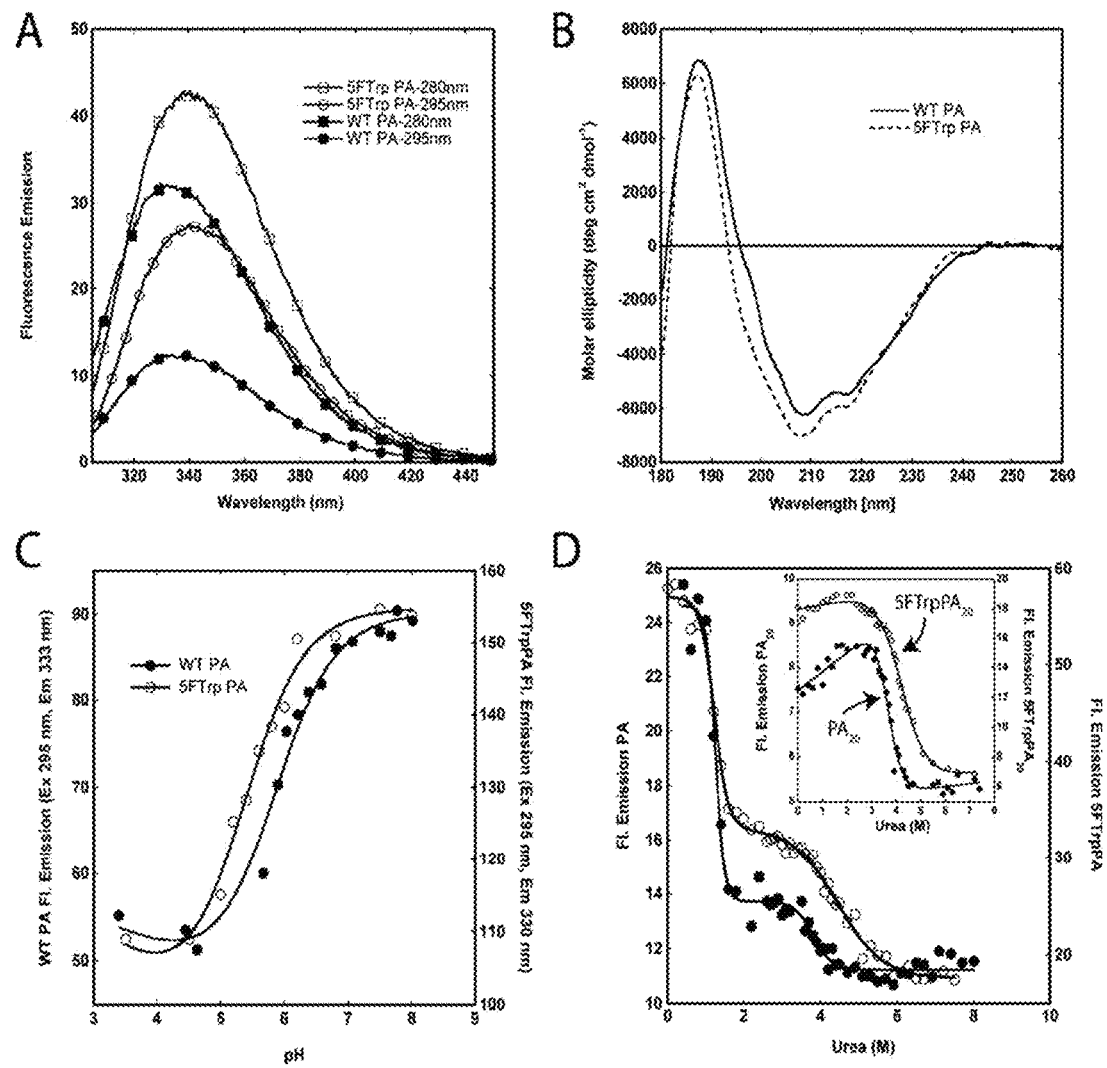
FIG. 1 shows graphs demonstrating the effect of 5-FTrp labeling on the spectroscopic properties and stability to urea and pH of PA. (A) Emission spectra (excitation at 280 or 295 nm) of WT PA and 5-FTrpPA. (B) Circular dichroism spectra of WT (—) and 5-FTrpPA (---). (C) Unfolding of WT and 5-FTrpPA as a function of pH. (D) Unfolding of WT (•) and 5-FTrpPA (○) as a function of urea concentration. The inset shows unfolding of $PA_{20}$ and 5-FTrp $PA_{20}$. Solid lines represent nonlinear least-squares fits to the data.

In more detail, described herein are methods of stabilizing PA, pharmaceutical compositions comprising stabilized PA complexes, vaccines, antitoxins, and therapeutic and prophylactic uses thereof. In particular, the invention is directed towards PA formulations with improved stability that do not require use of a cold chain for storage.

In one or more embodiments, described herein are stabilized PA complexes comprising (consisting essentially or even consisting of) PA and capillary morphogenesis protein-2 (CMG2). In one or more embodiments, CMG2 and PA interact along a binding interface, with direct interaction with CMG2 at His616 in domain 4, and indirect interaction at His211 and His253 in domain 1', such that a stabilized conformation of the PA protein is achieved in the PA-CMG2 complex. In one or more embodiments, the stabilized PA complex comprises an altered $pK_a$ of His86 in the $PA_{20}$ domain of PA in the complex. In one more embodiments, PA in the complex is modified such that the PA has decreased flexibility in the domain 2-domain 4 interface as compared to an uncomplexed PA protein. Thus, references herein to PA being "stable" or "stabilized" mean that the PA in the inventive complex has been made resistant to change from its "initial form" (defined as the original phenotype of the same PA before complexation). Thus, in the invention the PA in the complex is stabilized thermodynamically and/or physically/structurally, and/or is resistant to proteolysis and/or premature degradation of the protein in vivo after administration.

Wild type PA can be used in the complex, as well as PA having fluorinated histidine residues (such as those described in U.S. Pat. No. 7,731,979, incorporated by reference herein in its entirety), and mutated forms of PA having affinity for CMG2. In one or more embodiments, at least isolated $PA_{20}$ (residues 1-167) domain is used in the complex. In one or more embodiments PA83 is used in the complex. In one or more embodiments, the protective antigen for use in the complex is isolated from the other *B. anthracis* exotoxins. In some embodiments, the stabilized protective antigen complex itself is preferably free of edema factor (EF) and/or lethal factor (LF). That is, the immunogenic component in the stabilized complex against *B. anthracis* preferably consists of the (isolated) protective antigen protein, although it will be appreciated that EF and/or LF may be included in the compositions separate from the stabilized complex itself. In one or more embodiments, the PA is a polypeptide that is at least 80%, preferably at least 90%, more preferably at least 95%, still more preferably at least 97%, or most preferably at least 99% identical to GenBank AF306778 (SEQ ID NO. 1), which is incorporated by reference. In one or more embodiments, the polypeptide is encoded by SEQ ID NO:2, or a sequence having at least 80%, preferably at least 90%, more preferably at least 95%, still more preferably at least 97%, or most preferably at least 99% identical to SEQ ID NO:2. The polypeptide may be encoded by the PA gene that was reported by Vodkin et al., Cloning of the protective antigen gene of *Bacillus anthracis*, Cell 34 693-697 (1983). The polypeptide can be at least 97%, most preferably at least 99%, and most preferably identical to wild-type PA characterized by Miller et al., Anthrax Protective Antigen. Prepore-to Pore Conversion, Biochemistry 38(β2) 10432-10441 (1999), UniProt:Swiss-Prot: P13423 (SEQ ID NO:3), which is incorporated by reference, or any naturally-occurring (wild type) PA polypeptide from a strain of *Bacillus anthracis*. The PA polypeptide may be cloned and expressed in a heterologous host such as *Escherichia coli* or *Bacillus subtilis*. It is understood that homologs and analogs have the characteristics of the anthrax PA described herein and may be used in the methods of the invention. The term also includes any recombinant *B. anthracis* PA, or other modified form (variant).

The CMG2 for use in the invention preferably comprises, consists essentially, or even consists of purified forms of CMG2, and in particular, artificially (in vitro) expressed and/or synthetically created forms of CMG2 that have been purified for use in the complex. In other words, the CMG2 for use in the complex is not a naturally occurring or naturally-derived CMG2 from an in vivo source. In one or more embodiments, the CMG2 for use in the invention comprises (consists essentially or even consists of) SEQ ID NO:4. In one or more embodiments, CMG2 for use in the invention comprises at least the von Willebrand factor A (vWA) domain (residues 38-218) of CMG2 (Uniprot: P58335, Isoform 1, incorporated by reference herein; SEQ ID NO:4). In one or more embodiments, the CMG2 for use in the invention comprises (consists essentially or even consists of) residues 225-406 of SEQ ID NO:5. In one or more embodiments, CMG2 for use in the invention consists essentially of the vWA domain or even consists of the vWA domain of CMG2 (i.e., in lieu of the full length protein), or functional fragments thereof. In one or more embodiments, the CMG2 may be labeled (e.g., with a fluorinated residue).

The PA-CMG2 complexes are useful as both a vaccine and an antitoxin, providing epitopes for the production of antibodies against PA, but preventing key steps in pathogenesis (pore formation, translocation). The PA-CMG2 complexes in the invention have increased thermal stability, and in particular may have improved thermal stability that is about 20° C. higher than the thermal stability of uncomplexed PA. The PA-CMG2 complexes also have reduced rates of proteolysis by thermolysin. The CMG2 also reduces premature degradation of the PA protein, allowing a higher proportion of PA to be present for interacting with the host immune system.

Pharmaceutical compositions comprising the PA-CMG2 complex are also contemplated herein. Those skilled in the art will appreciate that depending on the intended mode of administration, the PA-CMG2 complex can be in various pharmaceutical compositions. The compositions will comprise the PA-CMG2 complex in a therapeutically effective amount in combination with a pharmaceutically acceptable carrier and, in addition, may include other medicinal agents, pharmaceutical agents, carriers, adjuvants (immunopotentiating agents), diluents, etc. As used herein, the term "pharmaceutically acceptable" means not biologically or otherwise undesirable, in that it can be administered to a subject without excessive toxicity, irritation, or allergic response, and does not cause unacceptable biological effects or interact in a deleterious manner with any of the other components of the composition in which it is contained. A pharmaceutically-acceptable carrier would naturally be selected to minimize any degradation of the compound or other agents and to minimize any adverse side effects in the subject, as would be well known to one of skill in the art.

The immunogenic compositions of the present invention may be formulated by dispersing the PA-CMG2 complex in the desired amount in any pharmaceutical carrier suitable for use in vaccines. Any pharmaceutical carrier suitable for administration to mammals which does not interfere with the immunogenicity of the modified PA protein may be employed. Exemplary carriers include aqueous solutions such as normal (n.) saline (~0.9% NaCl), phosphate buffered saline (PBS), sterile water/distilled autoclaved water (DAW), various oil-in-water or water-in-oil emulsions, as well as dimethyl sulfoxide (DMSO) or other acceptable vehicles, and the like. The compositions can further include an antibody against lethal factor and/or an antibody against edema factor of *B. anthracis* dispersed in the carrier.

Methods for therapeutic and prophylactic use of the PA-CMG2 complexes are also contemplated herein. In one aspect, a method for inducing an immunogenic response in a subject is described, which comprises administering to the subject a therapeutically-effective amount of the PA-CMG2 complex. As used herein, a "therapeutically-effective" amount refers to the amount that will elicit the biological or medical response of a tissue, system, or subject that is being sought by a researcher or clinician, and in particular elicit some desired therapeutic or prophylactic effect as against the anthrax infection by preventing and/or inhibiting toxin activity and/or pathogenesis of the toxin (e.g., through infiltration across the cell membrane in the subject). One of skill in the art recognizes that an amount may be considered therapeutically "effective" even if the condition is not totally eradicated or prevented, but it or its symptoms and/or effects are improved or alleviated partially in the subject.

Methods for inhibiting translocation of lethal factor or edema factor in a mammalian cell are also described, which comprise administering to the subject a therapeutically-effective amount of the PA-CMG2 complex. Methods for blocking pore formation in a cell expressing anthrax toxin receptor 2 are also described, which comprise administering to the subject a therapeutically-effective amount of the PA-CMG2 complex.

Compositions according to the embodiments disclosed herein are useful in treating and/or preventing anthrax infection by eliciting an immune response against *B. anthracis* in a subject. Thus, embodiments described herein have broad-spectrum therapeutic and/or prophylactic uses. The terms "therapeutic" or "treat," as used herein, refer to processes that are intended to produce a beneficial change in an existing condition (e.g., infection, disease, disorder) of a subject, such as by reducing the severity of the clinical symptoms and/or effects of the infection, and/or reducing the duration of the infection/symptoms/effects in the subject (who has already been infected). The terms "prophylactic" or "prevent," as used herein, refer to processes that are intended to inhibit or ameliorate the effects of a future infection or disease to which a subject may be exposed (but is not known to be currently infected with). In some embodiments, the vaccine is used as a postexposure prophylaxis countermeasure. In some cases the composition may prevent the development of observable morbidity from infection (i.e., near 100% prevention). In other cases, the composition may only partially prevent and/or lessen the extent of morbidity due to the infection (i.e., reduce the severity of the symptoms and/or effects of the infection, and/or reduce the duration of the infection/symptoms/effects). In either case, the compounds are still considered to "prevent" the target infection or disease, in the context of the present application.

In one or more embodiments, immunogenic compositions according to the invention can be used to induce protective immunity in the subject. The term "immunogenic" refers to the ability of the composition or its constituents to provoke an immune response in the subject after administration. The terms "protection" or "protective immunity" refers herein to the ability of the serum antibodies and cellular response induced during immunization to protect (partially or totally) against *B. anthracis* infection. Thus, a subject immunized by the pharmaceutical compositions or vaccines of the invention will experience limited growth and spread of the *B. anthracis* organism compared to an unvaccinated control.

In some embodiments, the subject is afflicted with or suffering from a condition (e.g., infection, disease, or disorder) before the compounds are administered, wherein methods described herein are useful for treating the condition and/or ameliorating the effects of the condition. A subject suffering from *Bacillus anthracis* infection may be identified by methods known in the art, e.g., by isolating *B. anthracis* from a biological sample (e.g., blood, respiratory secretions, etc.) from the subject. Symptoms of *B. anthracis* infection include fever (temperature greater than 100° F.), chills or night sweats, flu-like symptoms, cough, usually a non-productive cough, chest discomfort, shortness of breath, fatigue, muscle aches, sore throat, followed by difficulty swallowing, enlarged lymph nodes, headache, nausea, loss of appetite, abdominal distress, vomiting, or diarrhea or in the case of cutaneous contraction, a sore, especially on the face, arms or hands, that starts as a raised bump and develops into a painless ulcer with a black area in the center.

In other embodiments, the subject is free of observable signs of *Bacillus anthracis* infection before administering the composition, wherein the methods described herein are useful for preventing the occurrence or incidence of the condition and/or preventing the effects of the condition, as described above. In some embodiments, the subject is at risk of developing *Bacillus anthracis* infection. A subject suffering at risk of developing *Bacillus anthracis* infection may be identified by methods known in the art, e.g., by isolating *B. anthracis* from the blood, skin lesions, or respiratory secretions or by measuring specific antibodies in the blood.

The invention also relates to methods of using the PA-CMG2 complex(es), and/or compositions thereof, to induce serum antibodies against PA. The PA-CMG2 complex(es), and/or compositions thereof, are useful as vaccines to induce serum antibodies which are useful to prevent, treat, or reduce the severity of infections caused by *B. anthracis*, such as inhalation anthrax and/or cutaneous anthrax. The PA-CMG2 complex(es) of this invention are expected to induce a strong protective IgG antibody response in mammals, including humans.

The disclosed embodiments are suitable for various routes of administration, depending upon the particular carrier and other ingredients used. For example, the prophylactic and/or therapeutic compounds or compositions can be injected intramuscularly, subcutaneously, intradermally, or intravenously. They can also be administered via mucosa such as intranasally or orally.

In some embodiments, the compound or compositions can be provided in unit dosage form in a suitable container. The term "unit dosage form" refers to a physically discrete unit suitable as a unitary dosage for human or animal use. Each unit dosage form may contain a predetermined amount of the inventive compound (and/or other active agents) in the carrier calculated to produce a desired effect. The invention also relates to kits for vaccinating mammals for the treatment or prevention of *B. anthracis* infection in a mammal comprising the PA-CMG2 complex(es) of the invention.

The PA-CMG2 complex(es) of the invention can be co-administered with one or more other therapeutic or immunostimulatory agents. Further, the PA-CMG2 complex(es) can be administered before, after or concurrently with the agent or can be co-administered with other known therapies including anthrax vaccines, antibodies against LF, EF, PA, and *B. anthracis* antibiotics, e.g., amoxicillin, penicillin G procaine, ciprofloxacin, doxycycline, chloramphenicol, clindamycin, tetracycline, rifampin, and vancomycin.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

As used herein, "percent identity" between amino acid or nucleic acid sequences is synonymous with "percent homology," which can be determined using the algorithm of Karlin and Altschul (Proc. Natl. Acad. Sci. USA 87 2264-2268 (1990)), modified by Karlin and Altschul (Proc. Natl. Acad. Sci. USA 90 5873-5877, (1993)). Such an algorithm is incorporated into the NBLAST and XBLAST programs of Altschul et al., Basic Local Alignment Search Tool, J. Mol. Biol. 215 403-410, (1990). BLAST nucleotide searches are performed with the NBLAST program, score=100, wordlength=12, to obtain nucleotide sequences homologous to a nucleic acid molecule of the invention. BLAST protein searches are performed with the XBLAST program, score=50, wordlength=3, to obtain amino acid sequences homologous to a reference polypeptide (e.g., SEQ ID NO. 1). To obtain gapped alignments for comparison purposes, Gapped BLAST is utilized as described in Altschul et al., Gapped BLAST and PSI-BLAST: A new generation of protein database search programs, Nucleic Acids Res. 25 3389-3402 (1997). When utilizing BLAST and Gapped BLAST programs, the default parameters of the respective programs (e.g., XBLAST and NBLAST) are used which are available from the National Institutes of Health. A variant can also include, e.g., an internal deletion or insertion, a conservative or non-conservative substitution, or a combination of these variations from the sequence presented. In any event, it will be appreciated that fragments of the sequences described herein must remain "functional" as compared to the original sequence. Thus, the term "functional fragment" refers to sequences that may include insertion, deletions, and the like, but which nonetheless comprise or encode for a protein that retains the functionality of the original sequence (e.g., original binding specificity or ability, etc.).

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Example 1

$^{19}$F Nuclear Magnetic Resonance and Crystallographic Studies of 5-Fluorotryptophan-Labeled Anthrax Protective Antigen and Effects of the Receptor on Stability In this study, we have labeled PA with 5-fluorotryptophan (5-FTrp) and have studied the impact of labeling on structure and stability, using tryptophan fluorescence, circular dichroism, X-ray crystallography, and $^{19}F$ nuclear magnetic resonance (NMR). We also determined the effect of receptor binding on the stability to pH and temperature using $^{19}F$ NMR. There are seven tryptophans located in two of the four domains of PA: domain 1 (residues 1-258), which includes the 20 kDa $PA_{20}$ domain formed after cleavage by furin C-terminal to Arg167 and includes Trp65, −90, −136, −206, and −226; and domain 2 (residues 259-487), which includes Trp346 and Trp477. Trp346 is part of the domain 2β3-2β4 loop and is closest to the CMG2 binding interface.

$^{19}F$ NMR is a powerful tool for studying the structure and function of proteins, as it provides residue-specific information about environmental perturbations around each fluorine nucleus. On the basis of our $^{19}F$ NMR studies, we show that the Trp346 resonance undergoes conformational exchange at low pH, with very little change in the other $^{19}F$ resonances, providing further support that the domain 2β3-2β4 loop is particularly sensitive to pH. In addition, we show that receptor binding stabilizes the Trp346 resonance to variations in pH and temperature along with other tryptophan residues that are more distant from the binding interface. Finally, we have determined the structure of 5-FTrp-labeled PA to 1.7 Å resolution, which exhibits nearly identical structural properties as the WT protein. Our studies highlight the use of $^{19}F$ NMR to follow structural changes at a residue-specific level in a relatively high molecular weight protein and the positive impact of receptor binding on global protein stabilization.

Experimental Procedures

Materials

Urea (electrophoresis grade) and 5-fluorotryptophan were obtained from Sigma (St. Louis, Mo.). The urea concentration was determined by the refractive index at room temperature, and the urea was stored at −80° C. until the day of the experiment. All other chemicals prepared were reagent grade. *Escherichia coli* strain DL41 was obtained as a gift from the Yale *E. coli* genetic stock center.

Plasmid Construction and Mutagenesis

Plasmid pQE80-PA83 was used for generating mutations within the PA sequence. We used the following forward primers (SigmaGenosys, purified via high-performance liquid chromatography) to create the mutants and the corresponding reverse strands using the Quickchange mutagenesis kit from Stratagene:

| | |
|---|---|
| Trp206Tyr | CGGTTGATGTCAAAAATAAAAGAACTTTTCTTTCACCAT ACATTTCTAATATTCATGAAAAGAAAGG (SEQ ID NO: 6) |
| Trp226Phe | TCTCCTGAAAAATTCAGCACGGCTTCTGATCCGTACAGT GATTTCG (SEQ ID NO: 7) |
| Trp346Tyr | CATTCACTATCTCTAGCAGGGGAAAGAACTTACGCTGAA ACAATGGG (SEQ ID NO: 8) |
| Trp477Phe | GAGTGAGGGTGGATACAGGCTCGAACTTTAGTGAAGTGT TACCGC(SEQ ID NO: 9) |

Sequences were confirmed at the Protein Nucleic Acid Laboratory (PNACL) at Washington University in St. Louis (St. Louis, Mo.).

Protein Production

The pQE80-PA83 plasmid was transformed into *E. coli* tryptophan auxotrophic strain DL41 grown in the presence of 100 μg/mL ampicillin. Cells were grown in a defined medium that is identical to ECPM1, but substituting the casamino acids for defined amino acids. The tryptophan concentration was 0.25 mM. Cells were grown to an optical density (0D600) of 3.0 at 32° C. The cells then were washed twice with 0.9% NaCl; then the same medium containing 0.25 mM 5-FTrp in place of tryptophan was added to the cells, and the cells were resuspended. The cells were then incubated for 10 min prior to the addition of IPTG to a final concentration of 1 mM at 26° C., and grown for an additional 2-3 hours prior to harvesting.

Protein Purification

For the preparation of PA, after the OD had reached 6.0, bacterial cells were centrifuged and resuspended in a buffer containing 20 mM Tris-HCl (pH 8.0), 20% sucrose, and 1 mM EDTA for 15 min at room temperature. The cells were centrifuged for 15 min at 8000 g and 4° C., and the pellet was resuspended in ice-cold 5 mM MgSO4. Before centrifugation, 1 M Tris-HCl (pH 8.0) was added to a final concentration of 20 mM, and cells were again centrifuged at 4° C. (8000 g). The supernatant was filtered (0.2 μM, Millipore) and applied to a Hi-Trap Q anion exchange column pre-equilibrated in 20 mM Tris-HCl (pH 8.0) at 4° C. PA was eluted with a NaCl gradient on an Akta Prime LC system. Fractions were concentrated using an Amicon Ultra-15 10 kDa centrifugal filter (Millipore) and then applied to a Sephadex S-200 gel filtration column pre-equilibrated in 20 mM Tris-HCl and 150 mM NaCl (pH 8.0) at 4° C. Pure protein fractions were identified using sodium dodecyl sulfate-polyacrylamide gel electrophoresis (SDS-PAGE), pooled, and concentrated. CMG2 was prepared and purified as described previously (Rajapaksha et al. Monitoring anthrax toxin receptor dissociation from the protective antigen by NMR, Prot. Sci. 18, 17-23 (2009)). Briefly, a human cDNA corresponding to full-length CMG2 from Origene Technologies (Rockville, Md.) was used to clone the VWA domain of CMG2 (residues 38-218) into the expression plasmid pGEX-4T1, using BamH1-Not1 restriction sites as described previously (Wigelsworth et al. Binding stoichiometry and kinetics of the interaction of a human anthrax toxin receptor, CMG2, with protective antigen. J. Biol. Chem. 28; 279(22); 23349-56 (2004), incorporated by reference herein). pGEX-4T1 places a thrombin cleavable site glutathione s-transferase in the amino terminus of the expressed protein. The full length sequence of GST-CMG2 is in SEQ ID NO:5, where residues 225-406 are CMG2. A GST column using thrombin for elution of protein by cleaving the CMG2 and glutathione tag was used for protein purification.

Purification of $PA_{20}$ was conducted using a trypsin nicking protocol, whereby 10 mg of PA or 5-FTrpPA was digested with 10 μg of Trypzean (Sigma) for 30 min at room temperature, followed by the addition of an excess of soybean trypsin inhibitor (100 μg) on ice. The $PA_{20}$ was purified over a H-Trap Q column equilibrated in 20 mM Tris (pH 8.5) and 1 mM $CaCl_2$, eluting with a NaCl gradient.

Fluorescence

Data were recorded on a Cary Eclipse spectrofluorimeter equipped with a Peltier cooling system, using an excitation wavelength of 280 or 295 nm with slit widths set at 5 nm for both excitation and emission. All measurements were taken at 20° C. in a 50 mM Tris/25 mM MES/25 mM acetic acid buffer system, using 1 μM for pH experiments and 0.8 μM for the urea denaturation experiments. For the pH and urea experiments, only 295 nm excitation was used, recording emission data for the WT at 330 or 333 nm for the 5-FTrp-labeled PA or $PA_{20}$ proteins, and the data are an average of five scans from 300 to 600 nm. All samples were incubated overnight at the respective pH or urea concentrations to allow for adequate equilibration. For the pH experiments, the solid lines through the data points are nonlinear least-squares fits of the data to the Henderson-Hasselbalch equation to give an apparent $pK_a$ for the pH transition. For the urea denaturation experiments, in the case of the full-length PA proteins, the data were fit to a three-state transition as described previously. For the $PA_{20}$ urea denaturation experiments, the denaturation curves were fit to a two-state model with sloping baselines according to the model described by Clarke and Fersht. The curves were fit using Kaleidagraph version 3.6 (Synergy Software, Reading, Pa.).

Circular Dichroism (Far UV) Measurements were performed using a Jasco J810 spectropolarimeter. Spectra were measured in 10 mM HEPES (pH 8.0) at a concentration of 8 μM, using a 0.1 cm path length cell. The response time was 2 s, and the scan rate was 20 nm/min.

$^{19}F$ NMR Spectroscopy

Spectra were acquired on a Varian INOVA 400 MHz spectrometer equipped with a tunable inverse detection probe. Spectra were recorded at 20° C. unless otherwise indicated, and sample concentrations were typically in the 200 μM range in 50 Tris/25 mM Mes/25 mM AcOH buffer (pH 8.0) with 10% D2O added for a field frequency lock. Spectra were acquired using a 90° pulse width and a recycle delay of 5 s and were referenced to an internal standard of 4-fluorophenylalanine as described previously. Spectra typically required >10000 transients for adequate peak visualization and were processed with 10 Hz of line broadening.

MTSL Spin-Labeling

The 5-FTrpPA Glu712Cys protein was expressed and purified. We added 1 mM DTT to the final MgSO4/Tris (pH 8.0) step in the isolation of periplasm, and column buffers for purification included 1 mM DTT. The 5-FTrpPA was purified and the DTT removed by loading the protein solution onto a PD-10 column equilibrated with buffer containing 20 mM HEPES (pH 7.25) and 150 mM NaCl and then eluted using the same buffer. Immediately after purification, a 10-fold molar excess of MTSL [S-(2,2,5,5-tetramethyl-2,5-dihydro-1H-pyrrol-3-yl)methyl methanesulfonothioate] in methanol was added for 30 min at room temperature; then an additional 10-fold molar excess of MTSL was added, and this solution was incubated overnight at 4° C. The next day, MTSL was removed using an S-200 gel filtration column equilibrated in 50 mM Tris/25 mM Mes/25 mM AcOH buffer (pH 8.0) at 4° C. The sample was split into two aliquots, each containing 207 μL of PA, 50 μL of D2O, 1 μL of 10 mM p-fluorophenylalanine, and 217 μL of 50 mM Tris/25 mM Mes/25 mM acetic acid buffer. To one tube was added 25 μL of water, and to the other was added 25 μL of 100 mM TCEP. The final PA concentration in each tube was 150 μM.

Crystallization and Data Collection

5-FTrpPA was concentrated to 10 mg/mL in 150 mM NaCl and 10 mM Tris (pH 8.0) for crystallization. Screeing was conducted in Compact Jr. (Emerald biosystems) sitting drop vapor diffusion plates at 20° C. using equal volumes of protein and crystallization solution. Plate-shaped crystals (~200 μm×100 μm) were obtained in 1 day from the Index HT screen (Hampton Research) condition E8 [35% (v/v) pentaerythritol propoxylate (5/4 PO/OH), 0.05 M HEPES (pH 7.5), and 0.2 M potassium chloride] equilibrated against 100 μL of the crystallization solution at 20° C. Single crystals were transferred to a fresh drop of the crystallization solution (Index E8), which served as the cryoprotectant, and frozen in liquid nitrogen prior to the collection of data. Initial X-ray diffraction data were collected in house using a Bruker Microstar microfocus rotating anode generator equipped with Helios MX multilayer optics and a Platinum-135 CCD detector. Data were processed using the Proteum2 software package (Bruker-AXS). High-resolution data were collected at the Advanced Photon Source IMCA-CAT beamline 17ID using a Dectris Pilatus 6M pixel array detector.

Structure Solution and Refinement

Intensities were integrated using XDS, and Laue class analysis and data scaling were performed with Aimless, which suggested that the highest-probability Laue class was mmm and space group P212121. The structure was determined by molecular replacement with Molrep using a previously determined structure of the protective antigen as the search model [Protein Data Bank (PDB) entry 3MHZ)] as the search model. The in-house X-ray diffraction data, processed to 2.2 Å resolution, were used for the initial structure solution and refinement, and the higher-resolution synchrotron data were used for refinement of the final model. Structure refinement using and manual model building were conducted with Phenix and Coot, respectively. TLS refinement was incorporated in the final stages to model anisotropic motion. Structure validation was conducted with Molprobity, and figures were prepared using the CCP4MG package. Coordinates and structure factors for 5-FTrpPA were deposited to the Protein Databank with the accession code 4NAM.

Results

PA was labeled with commercially available 5-FTrp using the tryptophan auxotroph DL41, and proteins were >95% labeled as determined by electrospray mass spectrometry (ESI-MS). To determine the effect of labeling on the structure and stability of PA, we compared labeled and unlabeled proteins by far-UV circular dichroism (CD) to compare secondary structural content and measured the stability of the proteins to urea and pH using fluorescence. The fluorescence emission spectrum (excitation at 280 or 295 nm) of WT PA and 5-FTrpPA at 1 μM in 50 mM Tris/25 mM Mes/25 mM AcOH buffer (pH 8.0) at 20° C. is shown in FIG. 1A. The spectrum of the 5-FTrp-labeled PA (5-FTrpPA) is red-shifted relative to that of the unlabeled WT by ~8 nm, with excitation at either 280 or 295 nm. We also observed an increase in the amplitude of the emission spectrum of 5-FTrpPA via excitation at 280 or 295 nm compared to that of the unlabeled WT protein, with an increase that is somewhat smaller than those observed in other studies labeling with this amino acid. FIG. 1B shows the CD spectra of WT (—) and 5-FTrpPA (---) at 8 μM in 10 mM Hepes/OH (pH 8.0) at 20° C. The CD spectra of the WT and labeled proteins were similar (FIG. 1B), except for the absence of a small shoulder in the 5-FTrpPA spectrum at 198 nm. We used fluorescence to determine if the stability of PA to pH and urea was affected by the incorporation of 5-FTrp (FIGS. 1C,D). FIG. 1C shows the unfolding of WT and 5-FTrpPA as a function of pH at 0.8 μM in 50 mM Tris/25 mM Mes/25 mM AcOH buffer at 20° C. Fluorescence data were acquired using an excitation wavelength of 295 nm, and solid lines through the data are fits to the Henderson-Hasselbalch equation. FIG. 1D shows unfolding of WT (•) and 5-FTrpPA (○) as a function of urea concentration. The inset shows unfolding of $PA_{20}$ and 5-FTrp $PA_{20}$. Data were collected in 50 mM Tris/25 mM Mes/25 mM AcOH buffer (pH 8.0) at 20° C., via excitation at 295 nm and collection of the emission intensity at 330 nm (unlabeled) and 333 nm (5-FTrp-labeled). The concentration of all proteins was 0.8 μM. Solid lines represent nonlinear least-squares fits to the data.

The unfolding of 5-FTrpPA as a function of pH is similar to that of the WT protein, with a $pK_{app}$ of 5.3 compared to a $pK_{app}$ of 5.8 for the WT protein. In contrast to pH unfolding, which exhibits a single transition, the unfolding of PA and 5-FTrpPA by urea at 20° C. and pH 8.0 exhibits two transitions, one with a midpoint (CM) at ~1 M urea and a second that occurs at a CM of ~4 M urea. The results from the pH and urea studies are summarized in Table 1.

The isolated $PA_{20}$ (residues 1-167) domain exhibits an unfolding transition that matches the second transition observed in the fluorescence unfolding of PA (inset of FIG. 1D), and thus, we assign the unfolding of the $PA_{63}$ region comprising domains 1' to domain 4 (residues 168-734; domain 1' includes residues from the furin cleavage site to the beginning of domain 2) to the first transition at 1 M urea and the unfolding of $PA_{20}$ to the second, smaller amplitude transition that occurs at ~4 M urea.

Figure 2:
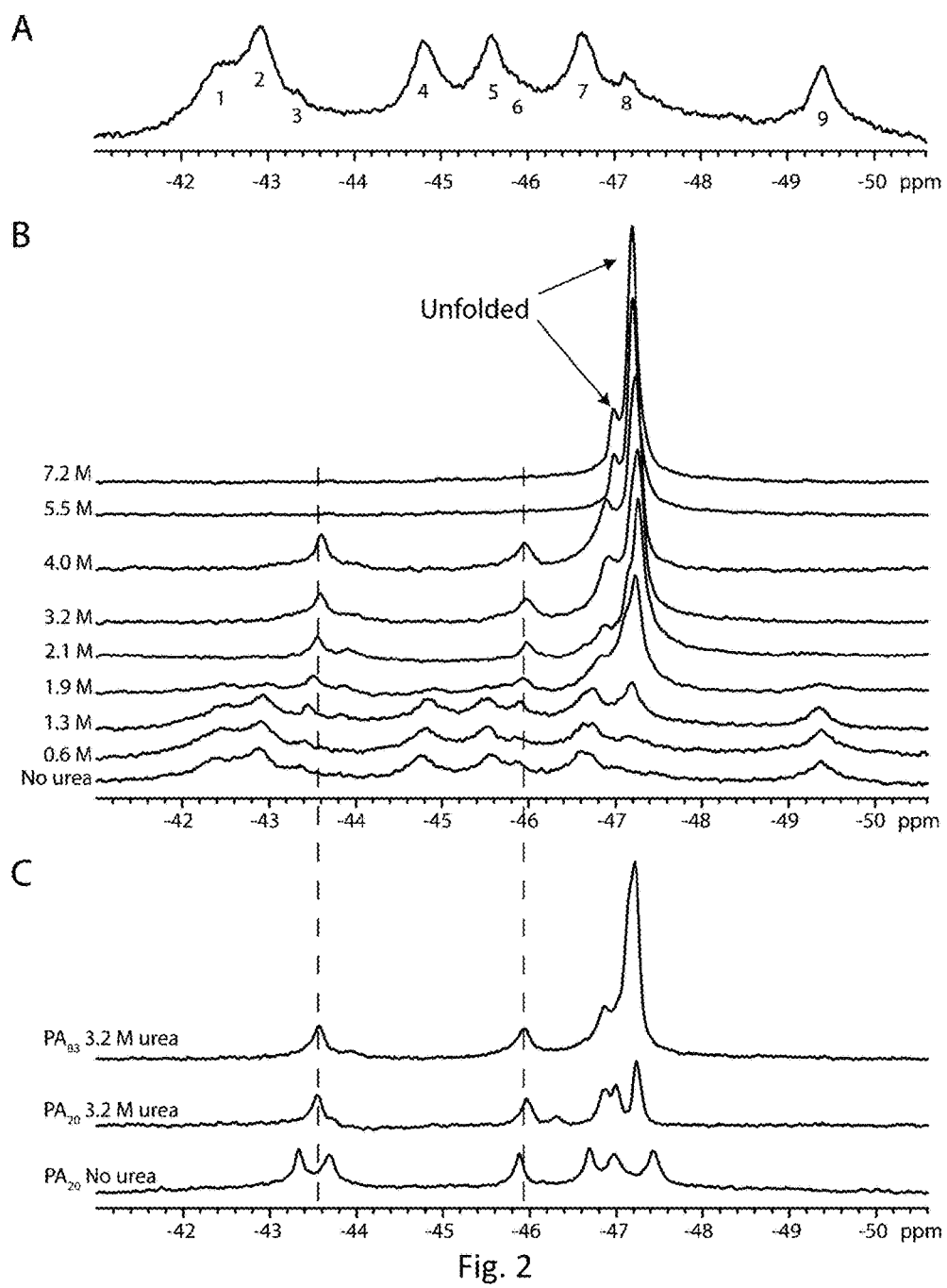
FIG. 2 shows graphs of $^{19}F$ NMR spectra for (A) 5-FTrpPA (230 μM); (B) Urea denaturation of 5-FTrpPA; and (C) Comparison of 19F NMR spectra of 5-FTrp $PA_{20}$ to that of full-length PA ($PA_{83}$) at 3.2 M urea.

Urea Unfolding of 5-FTrp-Labeled PA by NMR and Assignment of the $PA_{20}$ Resonances FIG. 2A shows the 400 MHz $^{19}$F NMR spectrum of 5-FTrpPA at pH 8.0 and 20° C. NMR spectrum of 5-FTrpPA (230 μM). This spectrum represents 12000 transients in 50 mM Tris/25 mM Mes/25 mM AcOH buffer (pH 8.0) with 10% $D_2O$. Data were referenced to an internal standard of 0.02 mM pF-Phe and processed with 10 Hz line broadening. The spectrum shows at least nine separate resonances with varying amplitudes and line widths over an ~8 ppm range. To make initial resonance assignments, we took advantage of the fact that urea denaturation occurs with two separate transitions and postulated that we may be able to identify those resonances that arise from $PA_{20}$ by following the resonances as a function of urea concentration (FIG. 2B). Urea denaturation of 5-FTrpPA as measured using $^{19}$F NMR is shown in FIG. 2B. Each spectrum represents 7000 transients recorded at 20° C. at 300 μM in 50 mM Tris/25 mM Mes/25 mM AcOH (pH 8.0) with 10% D2O. The amplitudes of resonances at −42.3, −42.9, −44.8, −45.6, and −49.4 ppm decrease, and those resonances disappear at ~1.9 M urea. However, the amplitudes of the small resonances at −43.4 and −45.8 ppm increase up to ~4 M urea, and then disappear at 5.5 M urea, consistent with the second transition observed in the fluorescence experiments. The amplitude of the resonance at −46.6 ppm increases, and the resonance shifts upheld to −46.8 ppm up to 4 M urea; then a second shift to −47 ppm is observed at 5.5 M urea. Because these latter resonances persist at higher denaturant concentrations and generally follow the second transition observed by fluorescence, we tentatively assigned these resonances to the $PA_{20}$ domain. The resonance at −47.2 ppm, the magnitude of which increases as the denaturant concentration is increased, was assigned to denatured resonances, because it resonates close to the frequency for free 5-FTrp (−47 ppm). Because the spectrum is not proton-decoupled, we could not distinguish individual resonances in the unfolded state at high urea concentrations, and therefore, this resonance likely encompasses the sum denatured states of a majority of the labeled tryptophans.

On the basis of these observations, we assigned the resonances that disappear at ~2 M urea to that of the $PA_{63}$ region and the remaining folded resonances that persist up to 4 M urea to the $PA_{20}$ domain. To confirm this assignment, we conducted limited proteolysis of the labeled PA with trypsin, which can be used in lieu of furin to cleave $PA_{20}$ from $PA_{83}$, isolated $PA_{20}$, and compared the resonances at 0 and 3.2 M urea to that of the WT protein (FIG. 2C). The $PA_{20}$ spectrum was recorded at 150 μM and represents 16000 transients recorded at 20° C. Note that the resonances in PA83 at −43.5, −46, and −46.8 ppm are at positions identical to those of $PA_{20}$. Data were referenced to an internal standard of 0.02

TABLE 1

Equilibrium Unfolding Thermodynamic Parameters of WT and 5-FTrp-Labeled PA and $PA_{20}{}^a$

| Experiment | $pK_{app}$ | $\Delta G°_{N\leftrightarrow I}$ (kcal mol$^{-1}$) | $\Delta G°_{I\leftrightarrow U}$ (kcal mol$^{-1}$) | $m_{N\leftrightarrow I}$ (kcal mol$^{-1}$ M$^{-1}$) | $m_{I\leftrightarrow U}$ (kcal mol$^{-1}$ M$^{-1}$) | $C_{M,N\leftrightarrow I}$ (M) | $C_{M,I\leftrightarrow U}$ (M) |
|---|---|---|---|---|---|---|---|
| WT PA | 5.8 ± 0.06$^b$ | 6.2 ± 0.9$^c$ | 9.1 ± 3.4 | 4.8 ± 0.7 | 2.4 ± 0.9 | 1.3 ± 0.02 | 3.8 ± 0.1 |
| 5-FTrpPA | 5.3 ± 0.05 | 3.8 ± 0.4 | 4.4 ± 0.5 | 3.2 ± 0.3 | 1.0 ± 0.1 | 1.2 ± 0.02 | 4.4 ± 0.2 |

| | | $\Delta G°_{N\leftrightarrow U}{}^d$ (kcal mol$^{-1}$) | | | $m_{N\leftrightarrow U}$ (kcal mol$^{-1}$ M$^{-1}$) | | $C_{M,N\leftrightarrow U}$ (M) |
|---|---|---|---|---|---|---|---|
| $PA_{20}$ | ND | 7.4 ± 1.1 | | | 2.0 ± 0.3 | | 3.7 ± 0.05 |
| 5-FTrp $PA_{20}$ | ND | 5.0 ± 0.4 | | | 1.2 ± 0.1 | | 4.2 ± 0.08 |

$^a$All data were recorded at 20° C. using a Cary Eclipse spectrofluorimeter.
$^b$Errors in $pK_{app}$ were determined by best fit to the Henderson-Hasselbalch equation, and errors in m and CM were obtained from nonlinear least-squares fitting of the data to a three-state model in Kaleidagraph.
$^c$Errors in $\Delta G°$ were determined using the relationship $[m^2(seC_M{}^2) \pm C_M{}^2(sem^2)]^{1/2}$, where $seC_M{}^2$ and $sem^2$ are the standard errors in $C_M$ and m, respectively.
$^d PA_{20}$ $\Delta G°$ values were determined for a single two-state N ↔ U transition with sloping baselines.

mM pF-Phe. First, the isolated PA$_{20}$ without urea exhibits six resonances for three tryptophans, suggesting these tryptophans are in slow chemical exchange. Although these resonances show differences in the number of peaks and chemical shifts relative to those of PA, the resonances observed at 3.2 M urea are nearly identical in chemical shift and intensity to that observed in the full-length protein. On the basis of this comparison, we assign the resonances from the native spectrum of PA (−43.4, −45.9, and −46.6 ppm) to that of PA$_{20}$.

Mutagenesis to Assign Resonances in the PA$_{63}$ Region

At this point, we decided not to pursue assignment of the PA$_{20}$ resonances by mutagenesis but rather focus on those resonances that would be found in the heptameric prepore state. To assign the resonances in the PA$_{63}$ region, we introduced relatively conserved mutations (Trp→Phe or Tyr) that in theory would not disrupt stability or folding and thus not perturb the $^{19}$F NMR spectrum; the mutation would result only in a loss of one of the resonance peaks. The following mutants were made: Trp206Tyr, Trp226Phe, Trp346Tyr, and Trp477Phe. We could not produce the labeled Trp226Phe and Trp477Phe proteins, probably because of an effect on the stability of the protein. Trp226 is relatively solvent exposed but is located ~5 Å from the two calcium ions in the structure, and the carbonyl of Trp226 forms a hydrogen bond with the amide hydrogen of Asp235, which coordinates one of the calcium ions. Thus, a tryptophan at position 226 may provide a necessary conformational constraint for calcium binding that cannot be achieved if this residue is a phenylalanine. Trp477 is near the N-terminus of the domain 2α3 helix that bridges interactions with domain 3, and local contacts around Trp477 include Pro232 and Tyr233 (domain 1') and Pro260, Pro373, and Ileu459 (domain 2), forming a hydrophobic pocket. A phenylalanine at this position may disrupt the local van der Waals contacts, potentially destabilizing contacts that span a range of ~200 residues.

Figure 3:
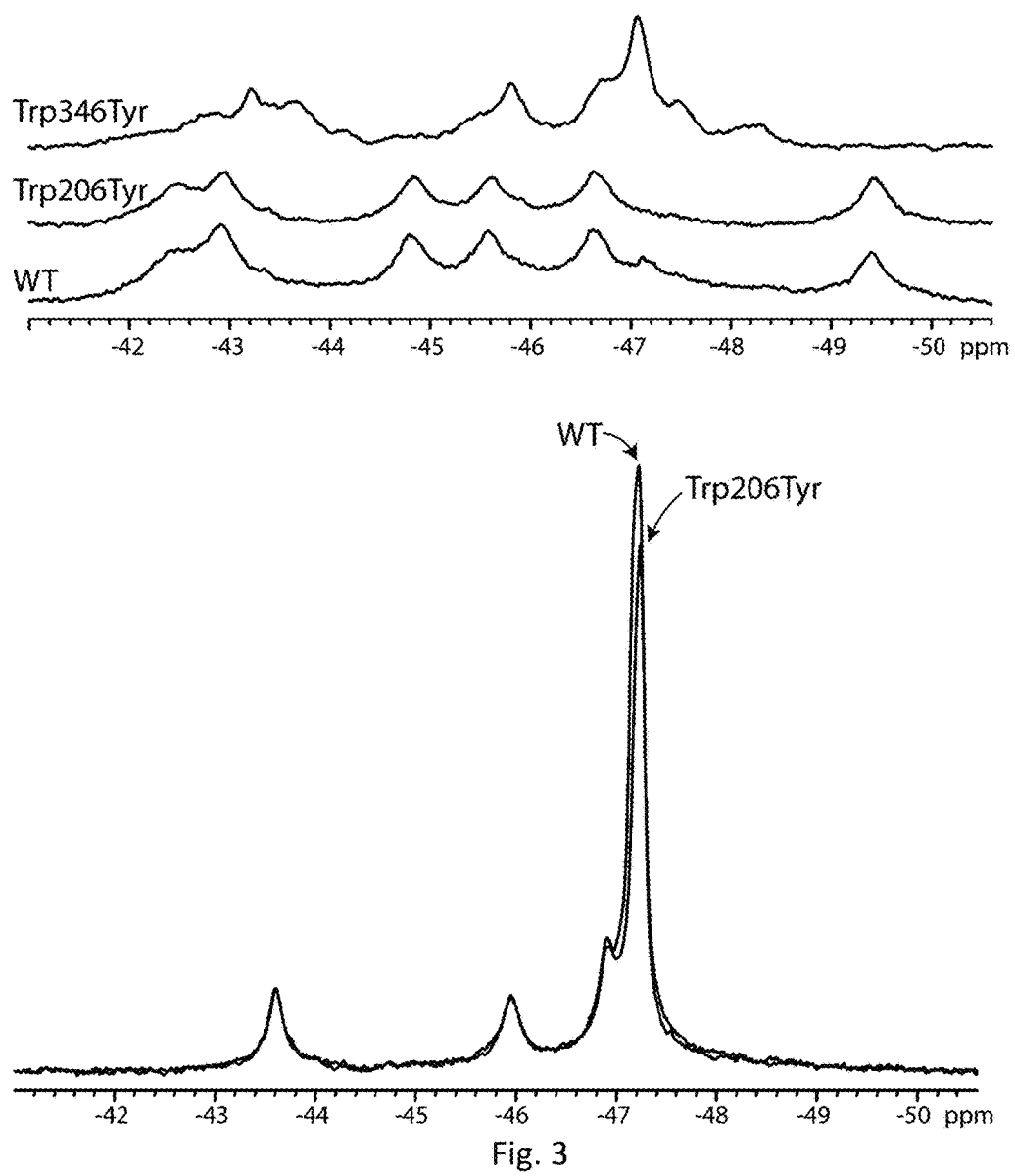
FIG. 3 shows $^{19}F$ NMR spectra of (A) WT PA, Trp206Tyr PA, and Trp346Tyr PA; and (B) Comparison of WT and Trp206Tyr at 3.2 M urea.

We could produce the labeled Trp346Tyr, but only at very low levels. In initial experiments, we tried labeling the Trp346Phe mutant for which we have a three-dimensional crystal structure; however, this labeled protein proved to be too unstable, and we could not accumulate enough pure protein for a spectrum. We were able to obtain enough labeled protein for a spectrum of Trp346Tyr (FIG. 3A), but this mutant was also unstable and showed significant chemical shift changes in the native spectrum that made assignment of this resonance difficult. (Data were recorded at 20° C. and 230 μM (WT), 250 μM (Trp206Tyr), or 200 μM (Trp346Tyr) in 50 mM Tris/25 mM Mes/25 mM AcOH buffer (pH 8.0) with 10% D$_2$O. Spectra represent 12000, 11000, and 14000 transients, respectively, with a 5 s relaxation delay. We note that the resonance at −49.5 ppm is missing; however, this may have shifted downfield to the new resonance that appears at −48 ppm.

The Trp206Tyr protein exhibits a spectrum that is nearly identical to that of the WT labeled protein, and the only loss in intensity that we observe is the loss of the small peak at −47.2 ppm (FIG. 3A). We had initially assigned this resonance to a partially denatured form of PA that exists in the absence of denaturant (FIG. 3A) but may be due to the Trp206 resonance. In any case, the lack of resonance intensity for this tryptophan suggests that Trp206 may be undergoing moderately fast chemical exchange, which could result in significant line broadening. Consistent with this notion, the B factors in this region are typically high across crystal structures of PA determined to date, suggesting that this residue may be able to sample multiple conformational environments.

To determine whether the line broadening of Trp206 was due to factors that depended on the protein conformation, we purified both the labeled PA and Trp206Tyr proteins and partially denatured these at 3.2 M urea, which is at the midpoint between the two identified transitions. The addition of denaturant to the approximate midpoint of the transition should lead to unfolded resonances corresponding to Trp206, -226, -346, and -477, while the resonances corresponding to PA$_{20}$ should remain largely folded. For Trp206Tyr, the unfolded resonance should exhibit a smaller amplitude, corresponding to the loss of a single fluorine. At 3.2 M urea, we observe a major resonance at −47.2 ppm, and three smaller resonances (−43.6, −46, and −47 ppm) (FIG. 3B). Both are at 150 μM and 16000 transients. Data were referenced to an internal standard of 0.02 mM pF-Phe. The three smaller resonances we attribute to the PA$_{20}$ domain (see FIG. 3B for comparison). Importantly, at 3.2 M urea, we observe a loss in the unfolded resonance intensity, likely due to the loss of a fluorine resonance from the Trp206Tyr mutation.

Crystallization of the 5-FTrp-Labeled W206Y Mutant

Figure 4:
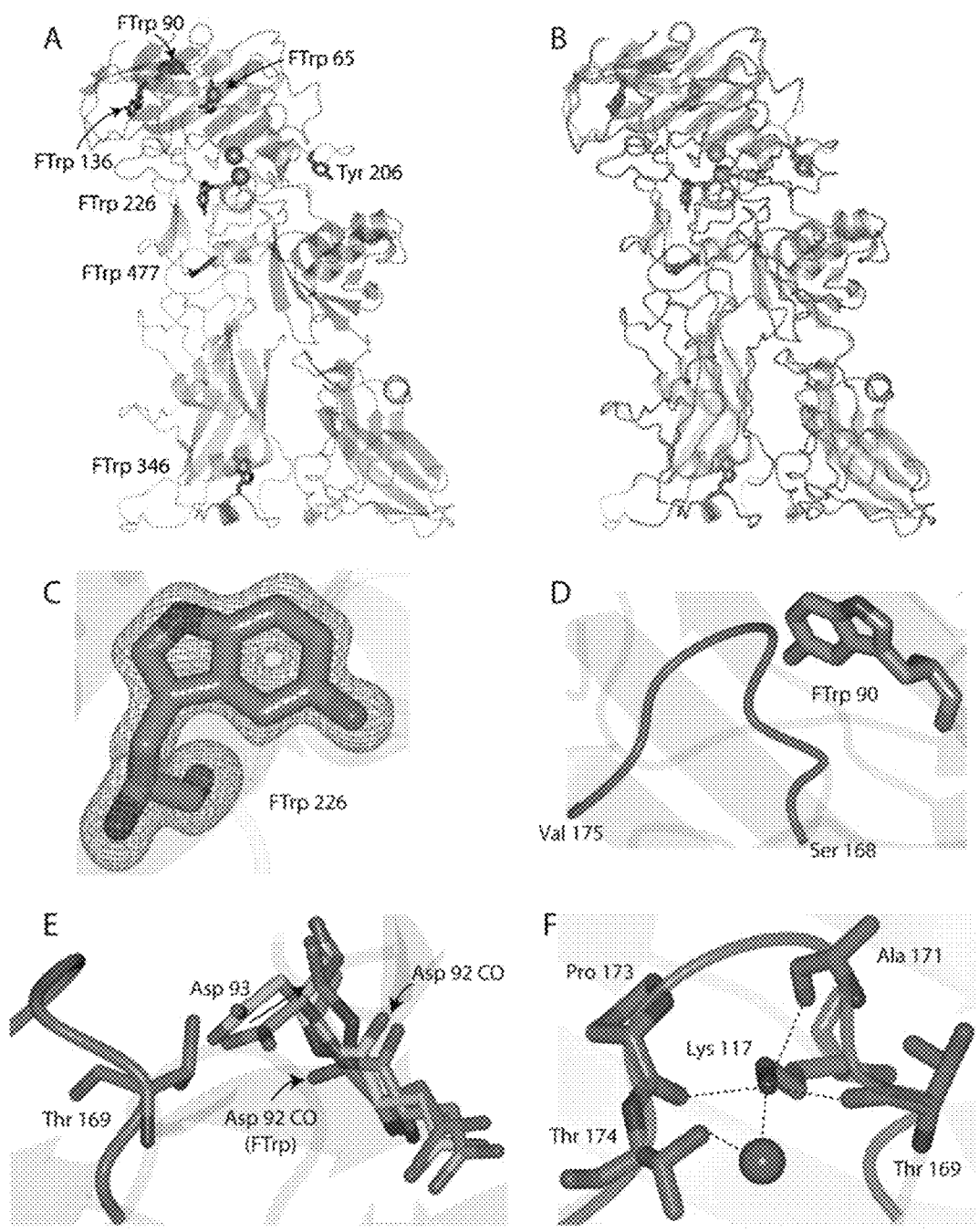
FIG. 4 shows the (A) X-ray crystal structure of 5-FTrpPA (Trp206Tyr) refined to 1.7 Å resolution, including 5-fluorotryptophan (FTrp) (gray) and Tyr206 residue are represented as cylinders, $PA_{20}$ portion of domain 1 (magenta), domain 1' (orange), domain 2 (green), domain 3 (blue), domain 4 (cyan), domain 2β2-2β4 loop that contacts the receptor (red), and Ca2+ ions (gold spheres); (B) Superposition of WT PA (PDB entry 3Q8B) drawn in worm style (gray), with Trp residues in WT PA (green); (C) Representative electron density map (Fo−Fc omit) for residue FTrp 226 contoured at 3σ. (D) Loop spanning Ser168-Val175 that could be traced to the electron density in the current structure. (E) Thr169 in the PA 5-FTrp structure (magenta) would clash with Asp93 as shown for PDB entries 3MHZ (green) and 3Q8B (cyan). (F) Contacts between Lys117 and the Ser168-Val175 loop.

To further determine if there are structural changes upon labeling, we crystallized the W206Y mutant, the structure of which was determined to 1.7 Å resolution. The structure is shown in FIG. 4, and data collection and refinement statistics are listed in Table 2.

TABLE 2

| Crystallographic Data for Protective Antigen 5-FTrp (W206Y) | |
|---|---|
| Data Collection | |
| unit cell parameters (Å) | a = 71.30, b = 93.95, c = 117.70 |
| space group | P2$_1$2$_1$2$_1$ |
| resolution (Å)$^a$ | 46.98-1.70 (1.73-1.70) |
| wavelength (Å) | 1.0000 |
| temperature (K) | 100 |
| no. of observed reflections | 348394 |
| no. of unique reflections | 86339 |
| ⟨I/σ(I)⟩$^a$ | 12.4 (1.8) |
| completeness (%)$^a$ | 99.8 (99.0) |
| multiplicity | 4.0 (4.1) |
| Rmerge (%)$^{a,b}$ | 6.6 (71.7) |
| Rmeas (%)$^{a,d}$ | 7.6 (83.5) |
| Rpim (%)$^{a,d}$ | 3.7 (39.8) |
| CC$_{1/2}$$^{a,e}$ | 0.998 (0.792) |
| Refinement | |
| resolution (Å)$^a$ | 46.98-1.70 |
| no. of reflections (working/test)$^a$ | 78632/4149 |
| R$_{factor}$/R$_{free}$ (%)$^{a,c}$ | 17.9/20.9 |
| no. of atoms (protein/Ca$^{2+}$/water) | 5351/2/400 |
| Model Quality | |
| rmsd | |
| bond lengths (Å) | 0.009 |
| bond angles (deg) | 1.108 |
| average B factor (Å$^2$) | 27.4 |
| all atoms | |
| protein | 27.2 |
| Ca$^{2+}$ | 13.5 |
| Water | 29.6 |
| coordinate error (maximum likelihood) (Å) | 0.15 |

TABLE 2-continued

Crystallographic Data for Protective Antigen 5-FTrp (W206Y)

| | |
|---|---|
| Ramachandran plot (%) | |
| most favored | 96.9 |
| additionally allowed | 3.1 |

[a] Values in parentheses are for the highest-resolution shell.
[b] $R_{merge} = \Sigma_{hkl}\Sigma_i|I_i(hkl) - \langle I(hkl)\rangle|/\Sigma_{hkl}\Sigma_i I_i(hkl)$, where $I_i(hkl)$ is the intensity measured for the ith reflection and $\langle I(hkl)\rangle$ is the average intensity of all reflections with indices hkl.
[c] $R_{factor} = \Sigma_{hkl}||F_{obs}(hkl)| - |F_{calc}(hkl)||/\Sigma_{hkl}|Fobs(hkl)|$; $R_{free}$ is calculated in an identical manner using 5% of the randomly selected reflections that were not included in the refinement.
[d] $R_{meas}$ equals the redundancy-independent (multiplicity-weighted) $R_{merge}$. $R_{pim}$ equals the precision-indicating (multiplicity-weighted) $R_{merge}$.
[e] $CC_{1/2}$ is the correlation coefficient of the mean intensities between two random half-sets of data FIG. 4A shows the X-ray crystal structure of 5-FTrpPA (Trp206Tyr) refined to 1.7 Å resolution. The positions of the 5-fluorotryptophan (FTrp) (gray) and Tyr206 residue are represented as cylinders. PA is colored as follows: magenta for the $PA_{20}$ portion of domain 1, orange for domain 1', green for domain 2, blue for domain 3, and cyan for domain 4. The domain 2β2-2β4 loop that contacts the receptor is colored red, and Ca2+ ions are shown as gold spheres. As seen in FIG. 4B, superposition of WT PA (PDB entry 3Q8B) drawn in worm style (gray). The Trp residues in WT PA are colored green. FIG. 4C shows a representative electron density map (Fo−Fc omit) for residue FTrp 226 contoured at 3σ. The structure overlays well with those of the WT and 2-FHis-labeled protein (PDB entries 3Q8B and 3MHZ, respectively), again indicating that 5-FTrp labeling only minimally perturbs the structure of the protein. However, there are some subtle structural changes and new contacts to the fluorine atoms that are formed, in particular within the $PA_{20}$ domain.

For example, when comparing the structure of 5-FTrp to those of the WT (PDB entry 3Q8B) and 2-fluorohistidine-labeled (PDB entry 3MHZ) forms, we noticed that particular regions could be traced to the electron density maps in the former that were disordered in the latter two structures. This includes the Lys72-Lys73 backbone, Glu51-Glu54, and the Ser168-Val175 loop. The Ser168-Val175 loop is in the proximity (3.5-4.0 Å) of Trp90 (FIG. 4D). This could be traced to the electron density in the current structure. This results in a conformational change in the nearby loop spanning Trp90-Gln94 relative to PDB entries 3Q8B and 3MHZ. Specifically, Asp93 moves away from the Ser168-Val175 loop as it would clash with Thr169, which results in a change in the backbone conformation at Asp92 (FIG. 4E). The PA 5-FTrp structure (magenta) would clash with Asp93 as shown for PDB entries 3MHZ (green) and 3Q8B (cyan). Therefore, Asp93 in PA 5-FTrp is moved away from the Ser168-Val175 loop as indicated by the arrow. Note that the side chain was disordered for Asp93 in the PA 5-FTrp structure. This results in a change in the backbone carbonyl conformation of Asp92 as indicated by the asterisks. This permits the formation of a water-mediated contact to the backbone carbonyl of Gln115. Stabilization of the Ser168-Val175 loop occurs by interactions with Lys117 as shown in FIG. 4F.

Assignment of the Trp346 Resonance Using PRE

Figure 5:
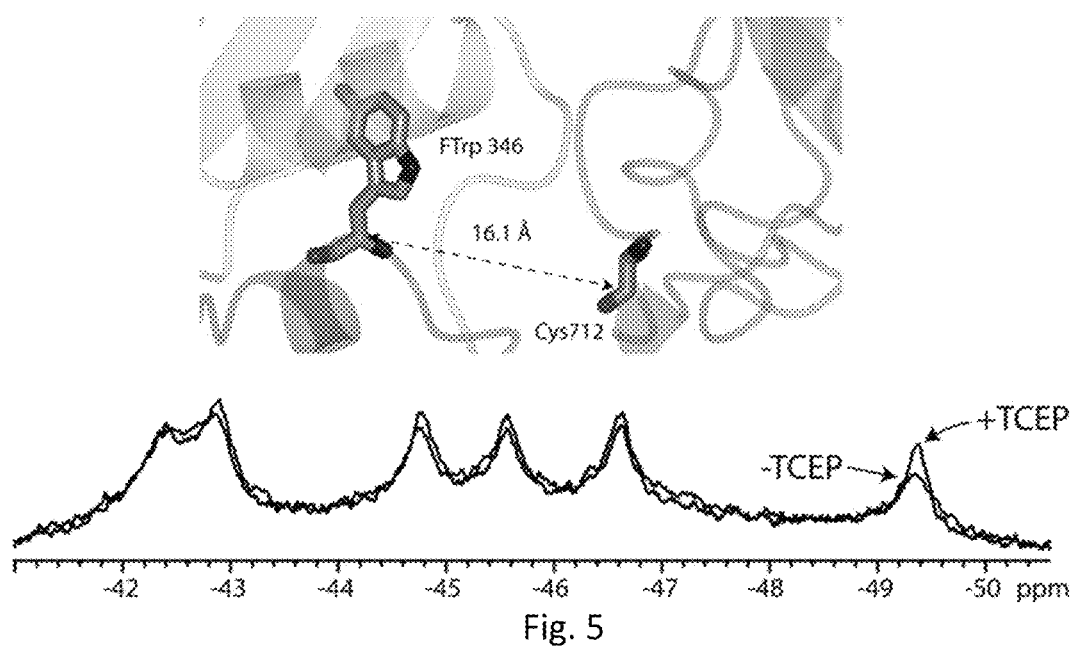
FIG. 5 shows an illustration and associated 19F NMR assignment through paramagnetic relaxation enhancement. Glu712Cys PA was labeled with the nitroxide spin-label MTSL. Cys712 is the only cysteine present in PA. The closest tryptophan to Cys712 is Trp346, and the Cα-Cα distance is 16.1 Å (top). Spectra with or without the reducing agent TCEP are shown.

Because of the instability of the Trp346Tyr mutant, we could not conclusively assign this resonance (FIG. 3) and thus used paramagnetic relaxation enhancement (PRE) to aid us in assigning this resonance. We did this by generating a cysteine mutant of a nearby residue located in domain 4, Glu712Cys. There are no cysteines naturally in PA, and thus the Glu712Cys mutant is the only residue available for labeling and does not affect the function of PA.(11, 35) The Cα-Cα distance between Glu712Cys and Trp346 is ~16 Å (FIG. 5), within the range for which PRE can be observed. We labeled Glu712Cys with MTSL [S-(2,2,5,5-tetramethyl-2,5-dihydro-1H-pyrrol-3-yl)methyl methanesulfonothioate] and compared the spectrum of MTSL-labeled PA to that of MTSL-labeled PA treated with TCEP, which reduces the paramagnetic nitroxide spin-label to a diamagnetic species. The $^{19}F$ NMR spectrum of MTSL-labeled PA, in the absence and presence of TCEP, is shown in FIG. 5. Cys712 is the only cysteine present in PA. The closest tryptophan to Cys712 is Trp346, and the Cα-Cα distance is 16.1 Å (top). Spectra with or without the reducing agent TCEP are shown. Data were recorded at 20° C. and 150 μM in 50 mM Tris/25 mM Mes/25 mM AcOH buffer (pH 8.0) with 10% D2O. Spectra represent 8800 transients, with a 5 s relaxation delay. Data were referenced to an internal standard of 0.02 mM pF-Phe. The resonance at −49.5 ppm exhibited the largest increase in amplitude in the presence of TCEP, and thus, we assigned this resonance to Trp346. Assignment of this tryptophan was also corroborated by measurements of pH sensitivity and receptor binding (see below).

$^{19}F$ NMR Experiments as a Function of pH

Figure 6:
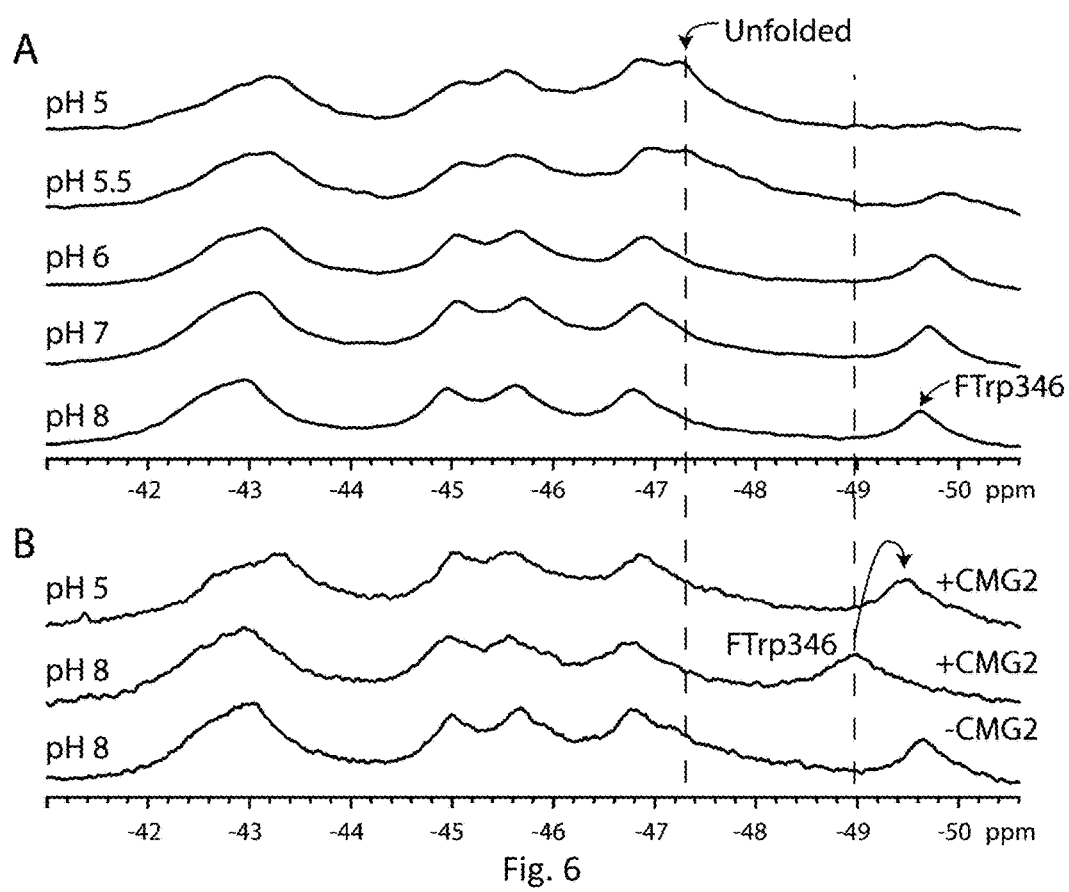
FIG. 6 shows the $^{19}F$ NMR spectra of 5-FTrpPA alone (A) and in the presence of the host receptor capillary morphogenesis protein 2 (CMG2) (B) as a function of pH.

FIG. 6A shows the effect of pH on the resonances of PA alone. The most dramatic change is the loss of the Trp346 resonance at low pH (pH 5), and this is most likely due to an increase in the level of chemical exchange. Spectra in panel A represent 12000 transients and were recorded at 5° C. and 250 μM in 50 mM Tris/25 mM Mes/25 mM AcOH buffer with 10% D2O and referenced to an internal standard of pF-Phe (0.02 mM). We did not observe a significant loss of the other remaining resonances, suggesting that this resonance alone was sensitive to pH. We also note that the intensity of the unfolded resonance at −47.2 ppm increases as the pH is lowered, which is concomitant with the decrease in intensity observed for the folded Trp346 resonance. We reasoned that, because the domain 2β3-2β4 loop binds in a groove on the receptor surface, receptor binding should result in an environmental change in Trp346. Furthermore, receptor binding results in stabilizing contacts to the domain 2β3-2β4 loop(13) and is known to stabilize the prepore against variations in pH that result in pore formation (pH 5-6), and thus, the Trp346 should be less prone to undergoing chemical exchange when it is bound to the receptor. In FIG. 6B, we compare spectra of PA alone and PA with a 2-fold excess of CMG2 at pH 8.0 and 5.0. In panel B, spectra represent 16000 transients and were recorded as described for panel A but with 150 μM 5-FTrpPA and 300 μM CMG2. There is a substantial chemical shift change in the Trp346 resonance (from −49.6 to −49 ppm) at pH 8.0, but very little change in the other resonances, again indicating that the resonance at −49.6 ppm is the Trp346 resonance. At pH 5, the resonance has moved to −49.4 ppm but remains visible, and there is a lack of a discernible unfolded resonance. This indicates that receptor binding has stabilized the protein to variations in pH.

$^{19}F$ NMR Experiments as a Function of Temperature

Figure 7:
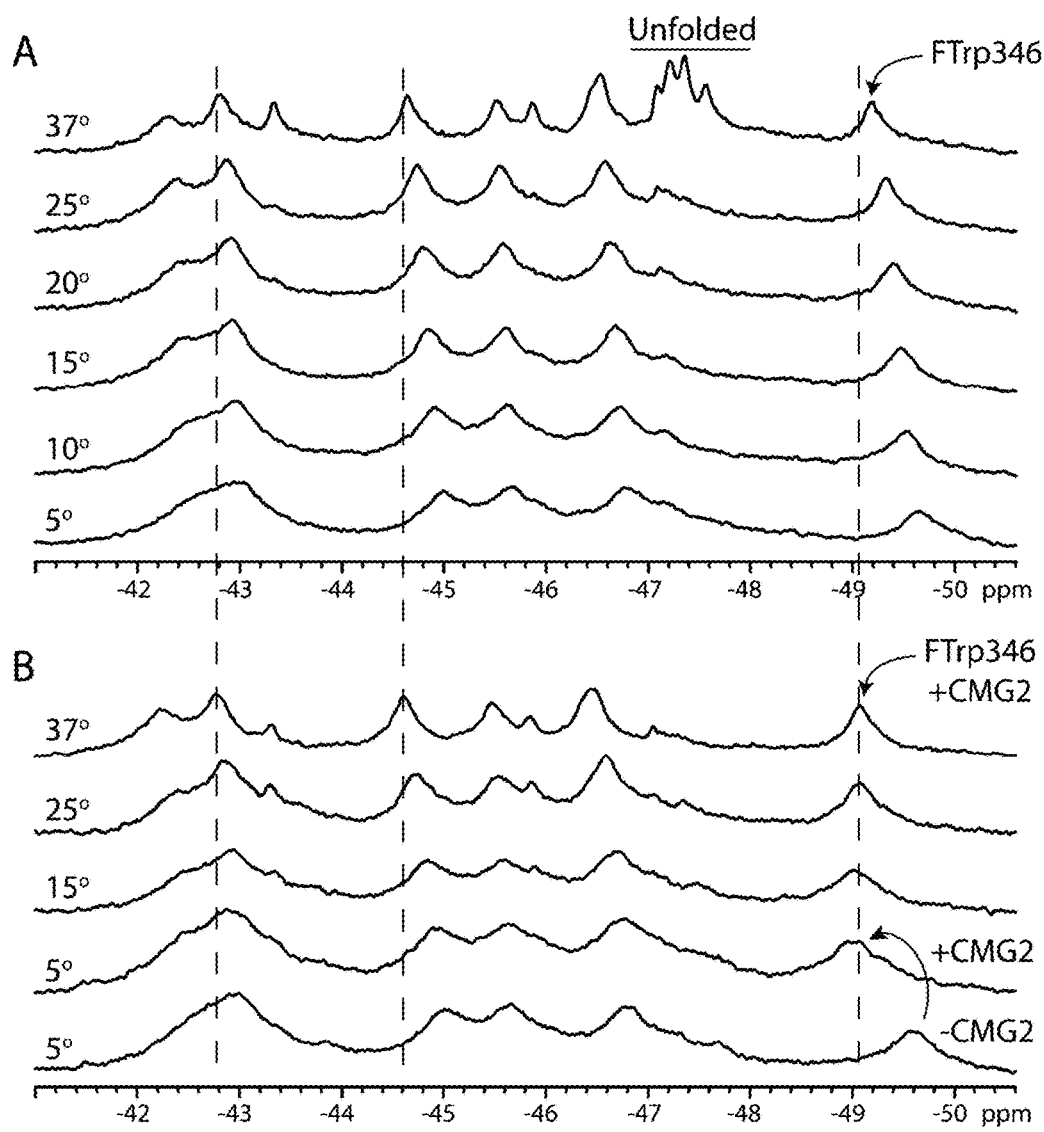
FIG. 7 shows $^{19}F$ NMR spectra of 5-FTrpPA alone (A) and in the presence of the host receptor capillary morphogenesis protein 2 (CMG2) (B) as a function of temperature.

We wanted to further explore the effect of receptor binding on the structure of the protein, focusing on the temperature dependence of the resonances. Our expectation was that the Trp346 resonance would experience an increase in the level of chemical exchange as the temperature increased, reducing the resonance amplitude. The results of our temperature experiments in the absence of receptor are shown in FIG. 7A and in the presence of receptor in FIG. 7B. Spectra in panel A represent 12000 transients at 250 μM in 50 mM Tris/25 mM Mes/25 mM AcOH buffer with 10%

D2O. In panel B, spectra represent 9000 transients and were recorded as described for A but with 300 μM 5-FTrpPA and 600 μM CMG2. Note the lack of an unfolded resonance at 37° C. in panel B compared to panel A. Data were referenced to an internal standard of 0.1 mM pF-Phe. In FIG. 7A, the amplitudes of two of the resonances that correspond to $PA_{20}$ (−43.4 and −45.9 ppm) undergo a sharp increase at 37° C. Also, at 37° C., the unfolded resonance (−47.2 to −47.6 ppm) appears as a broad peak with four distinct resonances. These are likely the unfolded resonances within the $PA_{63}$ region. For Trp346, this resonance experienced the largest chemical shift change, moving from −49.6 ppm at 5° C. to −49.2 ppm at 37° C. With the exception of the $PA_{20}$ resonances, the amplitude of the resonances decreased as the temperature increased, and by the same degree. Thus, Trp346 seemed to be as sensitive to temperature as the remaining $PA_{63}$ resonances.

In FIG. 7B, we added a 2-fold excess of the receptor CMG2 and conducted sets of experiments identical to that described in 7A. Again we observe the downfield shift in the Trp346 resonance when the receptor is bound, but as the temperature is increased, the Trp346 resonance does not shift any further. The major difference we observe is the significantly reduced amplitude of the unfolded resonances. Furthermore, while there is a small increase in the amplitudes of the two $PA_{20}$ resonances (−43.4 and −45.9 ppm), the increase is smaller than that observed in the absence of the receptor, suggesting that the effect of receptor binding is not simply a local effect but can be transmitted to residues within domain 1.

Discussion

PA undergoes several structural changes during the course of anthrax toxin pathogenesis, including receptor binding followed by oligomerization and endocytosis, and at acidic pH the formation of a membrane-spanning pore. In an effort to improve our understanding of these structural changes at a residue-specific level, we have conducted an initial study whereby we have biosynthetically incorporated 5-FTrp into the monomeric, 83 kDa form of PA and have used $^{19}$F NMR to probe the structure of the protein under a variety of conditions.

To determine the effect of fluorine labeling on the stability of the protein, we conducted pH and urea denaturation experiments, following unfolding by monitoring the changes in tryptophan fluorescence. The results of these experiments, which again are summarized in Table 1, suggest that while 5-FTrpPA is slightly more stable to acidic pH than the WT, the 5-FTrp-labeled PA or $PA_{20}$ domain exhibits a small decrease in the ΔG° of unfolding to urea, which seems mainly attributable to differences in the m values. However, an important caveat in the interpretation of these differences is the fact that the fluorescence properties of the 5-FTrp and Trp are different (see FIG. 1A), and the pre- and post-transition baselines are not well-defined. Clearly, further work is needed to elucidate the potential thermodynamic differences between the fluorine-labeled and unlabeled proteins.

We also report the 1.7 Å crystal structure of the 5-FTrp-labeled PA Trp206Tyr, and the structure shows some small differences in comparison to that of the WT protein, most notably the fact that we are able to observe regions of electron density that are missing in the WT structure. Importantly, both structures overlay well with one another (FIG. 4B), indicating that 5-FTrp labeling is minimally perturbing to the structure. Because the native state structures of the labeled and unlabeled proteins are similar, this lends strong support to the conclusions we draw with the 5-FTrp-labeled PA, that the effects that we observe by NMR (pH sensitivity and effects of CMG2 binding, for instance) are likely to be similar to that of the WT protein.

The ability to assign the Trp346 resonance, which lies near the interface between PA and CMG2, allowed us to probe how this resonance changes in the presence of the receptor and whether the Trp346 resonance is sensitive to variations in pH. The first crystal structure of PA postulated that the domain 2β3-2β4 loop was sensitive to pH and that at lower pH values the electron density within this region became disordered. We have also crystallized PA and compared structures a low and high pH; in some structures, we could observe an increase in the level of disorder at low pH (~5), whereas the WT protein, surprisingly, showed no increase in the level of disorder. We find that the resonance intensity of Trp346 specifically decreases as the pH is lowered, providing strong evidence that the domain 2β3-2β4 loop undergoes conformational exchange at low pH. The mechanism of the structural change that occurs in this loop as the pH is lowered has yet to be determined.

Receptor binding clearly has a stabilizing influence on the structure of the protein. While Trp346 undergoes a substantial chemical shift change (~0.6 ppm) upon receptor binding, we did not observe the same loss of intensity of this resonance either at low pH or at higher temperatures. Also, the unfolded resonance intensity is attenuated (low pH or higher temperatures) when the receptor is bound. The effects that we observe on the temperature dependence of the resonances suggest that the receptor stabilization is not only local to the binding interface but also more long-range. This effect is consistent with studies following histidine hydrogen-deuterium exchange kinetics, in which the rates of histidine hydrogen-deuterium exchange were slowed upon receptor binding, even for residues >40 Å from the binding interface.

The studies presented here provide an initial step toward following the conformational changes that occur in the anthrax toxin at low pH. On the basis of the experiments reported here, the feasibility of using $^{19}$F NMR to follow structural changes in PA is warranted. One important question we wish to address using this method is the order of events leading to the formation of a pore. It has been proposed that an initial step in the formation of the pore from the prepore state is the closure of the φ-clamp, a ring of phenylalanines (Phe427) located within the lumen of the pore that clamps down on its substrate (either edema factor or lethal factor) and is required for protein translocation. In initial experiments, we have used mutagenesis to replace this phenylalanine with a tryptophan and have labeled the protein with 5-FTrp, and we are able to observe this resonance (F-Trp427) in the prepore and pore states. Therefore, in the future, we should be able to follow this resonance during the process of pore formation in real time. In any case, $^{19}$F NMR opens the possibility of exploring structural changes in this protein at a residue-specific level.

Example 2

Long-Range Stabilization of Anthrax Protective Antigen Upon Binding to CMG2

Figure 8:
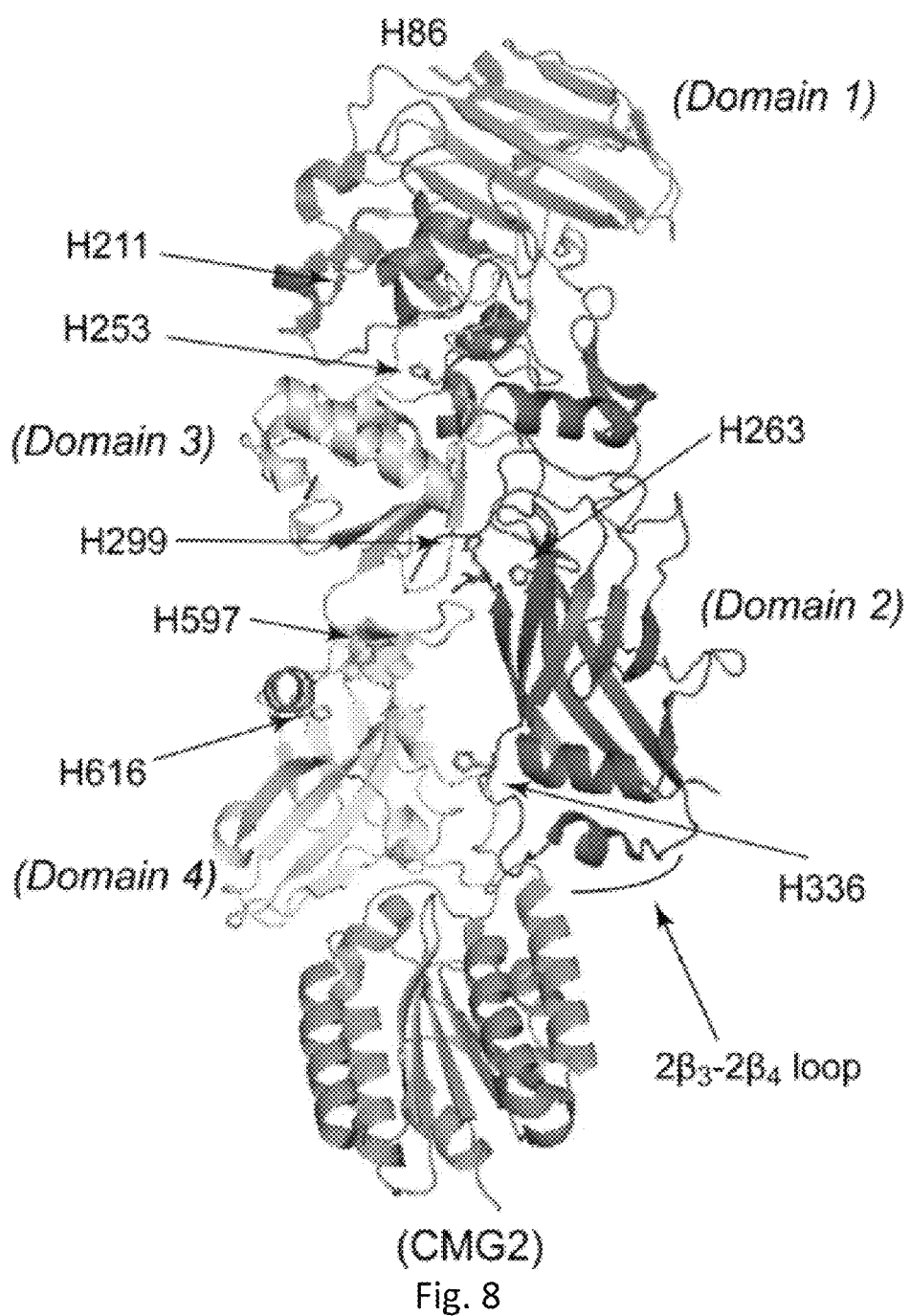
FIG. 8 is an illustration of the structure of the PA-CMG2 complex (PDB entry 1T6B). Eight histidine residues are shown (green sticks). Domain 1, Ser15-Ala258 (magenta); domain 2, Tyr259-Thr487 (blue); domain 3, Thr488-Arg595 (pink); domain 4, Phe596-Ile734 (yellow); vWA domain of CMG2 (orange).

PA binding to the host cell receptor capillary morphogenesis protein-2 (CMG2), either to the monomeric 83 kDa PA4 or the heptameric prepore. Both structural and biochemical studies of the PA-CMG2 complex indicate that the binding interface is comprised of domain 4 and a small loop from domain 2 (2β3-2β4 loop), which inserts into a groove on the surface of CMG2 (FIG. 8). The binding affinity between PA and CMG2 is very high (Kd~200 pM)7 and increases at acidic pH.8 At the same time, receptor binding has been shown to improve the stability of the heptameric form of PA to pH and to facilitate the internalization of the toxin-bound prepore.9,10 Our recent NMR study of PA labeled with 5-fluorotryptophan also suggested that receptor binding significantly stabilizes PA to both pH and temperature. FIG. 8 shows the structure of the PA-CMG2 complex (PDB entry 1T6B).

To further investigate the changes in stability of PA upon CMG2 binding, we used a histidine hydrogen-deuterium exchange (His-HDX) method, which monitors the slow rate of HDX of the $C_2$ hydrogen of the imidazole group of histidine, and followed the rate of HDX as a function of increasing concentrations of guanidinium hydrochloride (Gdn-HCl). Thus, using this method, we can measure the equilibrium unfolding of specific histidine residues within the protein. There are 10 histidine residues in PA that are scattered throughout the molecule, one in the $PA_{20}$ domain, two in domain 1', five in domain 2, and two in domain 4. Herein, we show that receptor binding leads to a significant shift in the concentration of Gdn-HCl required for full HDX (unfolding) of histidines located in separate domains, suggesting that receptor binding has a global effect on the thermodynamic stability of the protein. These studies are corroborated using fluorescence, in which we were able to probe selectively fluorescence changes in PA using a 4-fluorotryptophan-labeled von Willebrand factor A (vWA) domain of CMG2, which is nonfluorescent. His-HDX-MS also allowed us to determine the $pK_a$ and more accurate solvent accessibilities of the histidines in the presence and absence of the receptor and reveal differences in the microenvironment around the histidine residues as a consequence of receptor binding. Our results indicate that receptor binding has a profound long-range impact on the stability and structure of PA, suggesting that, with a limit on hinge-like motions between domain 2 and domain 4, the protein can be made to be significantly more stable. Because PA is the major antigenic component of the current anthrax vaccine, our studies would indicate that addition of CMG2 to a vaccine formulation could improve the stability and overall efficacy of the vaccine.

Materials and Methods

Materials

Deuterium oxide (D2O, 99%) was purchased from Cambridge Isotope laboratories (Andover, Mass.), and guanidine hydrochloride (Gdn-HCl), deuterium chloride (DCl), and sodium deuteroxide (NaOD) were from Sigma-Aldrich (St. Louis, Mo.). Lys-C was purchased from Wako Chemicals USA (Richmond, Va.); chymotrypsin and thermolysin were from Sigma-Aldrich, and Glu-C was from Worthington Biochemical (Lakewood, N.J.). All other chemicals and materials used were either reagent grade or of the highest quality commercially available.

Protein Expression and Purification

PA and the vWA domain of CMG2, encoding residues 38-218, were expressed and purified as described previously.(14-16) Labeling of CMG2 with 4-fluorotryptophan was conducted using the tryptophan auxotroph DL41 (provided as a gift from the Yale *E. coli* Genetic Stock Center). 4-Fluorotryptophan was purchased from Gold Biotechnology (St. Louis, Mo.).

Unfolding Experiments Followed by His-HDX

PA alone (0.5 nmol) and the PA-CMG2 complex (0.5 nmol of PA and 2.5 nmol of CMG2) were incubated in 100 μL of 100 mM HEPES (pH* 7.5) made with $D_2O$ containing 1 mM $MgCl_2$ and various concentrations of Gdn-HCl for 48 h at 37° C. The pH* of the buffer was adjusted with diluted NaOD with a Solution Analyzer model 4603 instrument (Amber Science, Eugene, Oreg.) equipped with a glass AgCl electrode (model 476086, Nova Analytics, Woburn, Mass.). The reported pH* values are direct pH meter readings of the $D_2O$ buffer solutions calibrated with standard buffer solutions made with $H_2O$ and are uncorrected for the isotope effect at the glass electrode. The reaction was stopped by adding 10 μL of formic acid, and the protein was freed from the salts using an Ultra Micro Spin C4 column (Nest Group, Southboro, Mass.) following the manufacturer's instructions and dried in a Speed Vac.

The protein was then redissolved in 60 μL of 100 mM ammonium bicarbonate and digested by 2 μg of Lys-C for 30 min at 25° C. The reaction was stopped by adding 10 μL of formic acid, and the digest was divided into three parts and then dried in a Speed Vac. Two parts were further digested, one part by 1 μg of Glu-C for 30 min and other part by 1 μg of chymotrypsin for 30 min. The resulting three digests were dried in a Speed Vac and redissolved in 30 μL of 0.1% trifluoroacetic acid (TFA). The three digests at particular Gdn-HCl concentrations were mixed and analyzed by liquid chromatography and tandem mass spectrometry (LC-MS/MS) using a Qstar quadrupole/time-of-flight mass spectrometer (Applied Biosystems-MDS Sciex, Foster City, Calif.) equipped with a TurbolonSpray ion source. The protein digests were injected into a reverse-phase C18 column (500 mm×0.1 mm, Waters); the peptides were chromatographed using a linear gradient of acetonitrile from 2 to 50% in aqueous 0.1% formic acid over a period of 40 min at a rate of 30 μL/min, and the elute was directly introduced into the mass spectrometer. The total ion current was obtained in the mass range of m/z 400-2000 in the positive ion mode with an acquisition time of 1 s for each scan.

The pseudo-first-order rate constant (k) of the HDX reaction was determined by monitoring changes in the ratios of the M+1/M isotopic peak of a given peptide before (time zero) and after (time t) the HDX reaction, and fitting the data to a first-order rate equation,(17) and the values were corrected upward to offset the decreased solvent concentration caused by the volume effect of Gdn-HCl. The relationship between solvent concentration and Gdn-HCl concentration was experimentally determined, from which the correction factor to correct the rate constant of the HDX reaction in Gdn-HCl solutions was obtained. The corrected HDX rate was plotted against the concentration of Gdn-HCl. From the plot, the midpoint (Cm) of the Gdn-HCl-induced unfolding transition was estimated by fitting the denaturation curve to a two-state model. The free energy change (ΔG°) in PA denaturation was estimated from the plot by calculating the equilibrium constant ($K_{eq}$) of denature/native protein at each Gdn-HCl concentration as follows.

$$K_{eq} = \frac{\text{fraction of } [D]}{\text{fraction of } [N]} = \frac{k - k^N}{k^D - k}$$

where k is the first-order His-HDX rate constant at a specific Gdn-HCl concentration, $k^N$ is the k for the native protein (k at 0 M Gdn-HCl), and $k^D$ is the k for the fully denatured protein (can be obtained from the plateau of the sigmoidal curve). The $K_{eq}$ value was used to determine the free energy change of denaturation at each Gdn-HCl concentration with the equation $$\Delta G° = -RT \ln K_{eq}$$

where R is the gas constant and T is the absolute temperature in kelvin. By plotting the ΔG° values against the concentrations of Gdn-HCl and extrapolating the fitted line to 0 M Gdn-HCl, we obtained ΔG° water in the absence of Gdn-HCl.

Unfolding Experiments Followed by Fluorescence Spectroscopy

PA alone and PA (1 μmol) complexed with 4-fluorotryptophan-labeled CMG2 (4-FTrpCMG2, 2 μmol) in 100 mM HEPES (pH 7.5) containing 1 mM $MgCl_2$ and various concentrations of Gdn-HCl were placed in a Cary-Eclipse fluorimeter, and the fluorescence emission spectra were recorded at 20° C. by exciting the tryptophan residues in PA at 295 nm and monitoring the emitted light at 334 nm. The data were fit to a three-state transition in the absence of CMG2 as described by Wimalasena, D. S. et al. ((2007) Effect of 2-fluorohistidine labeling of the anthrax protective antigen on stability, pore formation, and translocation. Biochemistry 46, 14928-14936.)

Pulse Proteolysis Assay

The method described by Young and co-workers was used to conduct the pulse proteolysis experiment. (Young, T. A. et al. (2007) Comparison of proteolytic susceptibility in phosphoglycerate kinases from yeast and E. coli: Modulation of conformational ensembles without altering structure or stability. J. Mol. Biol. 368, 1438-1447.)

PA (100 μg, 6 μM) or PA with 48 μg (12 μM) of CMG2 was incubated overnight at room temperature in 200 μL of 20 mM Tris buffer (pH 8.0) containing 150 mM NaCl, 10 mM $CaCl_2$, and 1 mM $MgCl_2$. The next day, 20 μL of 5 mg/mL thermolysin prepared in 2.5 M NaCl and 10 mM $CaCl_2$ was added to the 200 μL of PA and PA-CMG2 complex samples and incubated at room temperature for various periods of up to 120 min. Aliquots (15 μL) were withdrawn at the different time points, to which 5 μL of 50 mM EDTA and 4 μL of 6× SDS-PAGE sample buffer were added to stop the proteolysis. The solution was then boiled for 5 min, and 15 μL of the solution was run on a 15% SDS-PAGE gel.

pH* Titration Studies

PA (0.5 nmol) and the PA-CMG2 complex (0.5 nmol of PA and 2.5 nmol of CMG2) were placed in 100 μL of buffer with different pH* values (4.5-9.0) that contains 20 mM CHES, 20 mM HEPES, 20 mM MES, 50 mM NaCl, and 1 mM $MgCl_2$ and incubated for 50 h at 37° C. The pH* of the buffer was adjusted with diluted DCl or NaOD. The reaction was stopped by adding 5 μL of formic acid, and the protein was freed from the buffer salts using an Ultra Micro Spin C4 column (Nest Group) according to the manufacturer's instructions and dried in a Speed Vac. The protein was redissolved in 100 mM ammonium bicarbonate and digested with Lys-C alone, a combination of Lys-C and Glu-C, or a combination of Lys-C and chymotrypsin as described above. The resulting digests were dried in a Speed Vac, redissolved in 0.1% TFA, and then analyzed by LC-MS/MS using an LTQ-Orbitrap XL mass spectrometer. The pseudo-first-order rate constant (k) of the HDX reaction was determined as described above, and the k values were plotted as a function of pH*, from which the $pK_a$ of each histidine residue and the half-life ($t_{1/2}$) of the HDX reaction were determined.

Structural Analysis

A comparison of protein structures was performed using PyMOL (Molecular Graphics System software, DeLano Scientific, Palo Alto, Calif.). The structural data of PA (PDB entry 3Q8B) and the PA-CMG2 complex (PDB entry 1T6B) deposited in the Protein Data Bank were used in the comparison. The same structural data were used to obtain the ASA (solvent accessible surface are) values for the $C_2$ atoms of the histidine residues using GETAREA.

Results and Discussion

Stability of PA and PA Bound to CMG2

To investigate how the stability of PA changes upon binding to CMG2, we conducted Gdn-HCl-induced equilibrium unfolding experiments on PA alone and PA complexed with CMG2, using His-HDX-MS. Histidine residues in a protein that are protected (to at least a certain extent) from the solvent become exposed to solvent upon unfolding of the protein caused by increasing concentrations of Gdn-HCl, which subsequently increases the magnitude of HDX rates for the histidine residues as the protein unfolds. The histidine residues we monitored were His211, His253 (domain 1'), His336 (domain 2), and His616 (domain 4). Four peptides containing these four histidine residues, each containing one histidine residue, were detected by LC-MS/MS, and their precursor ion spectra were used to calculate the pseudo-first-order rate constants (k) for their HDX reactions.

During the study, it became apparent that the HDX rates obtained in the Gdn-HCl solution must be corrected upward. This is because the concentration of water in a highly concentrated Gdn-HCl solution (e.g., 5 M Gdn-HCl) is significantly lower than the concentration of water in a solution without Gdn-HCl. This means that the amount of a heavy water molecule ($D_2O$) available in such a solution in a defined volume is significantly small, causing us to underestimate the HDX rates. We determined the relationship between the water and Gdn-HCl concentrations in various concentrations of Gdn-HCl solutions, from which an equation to correct upward the experimentally obtained HDX rates was obtained (see the Supporting Information). All the HDX rates measured in Gdn-HCl solutions were corrected using this equation.

Figure 9:
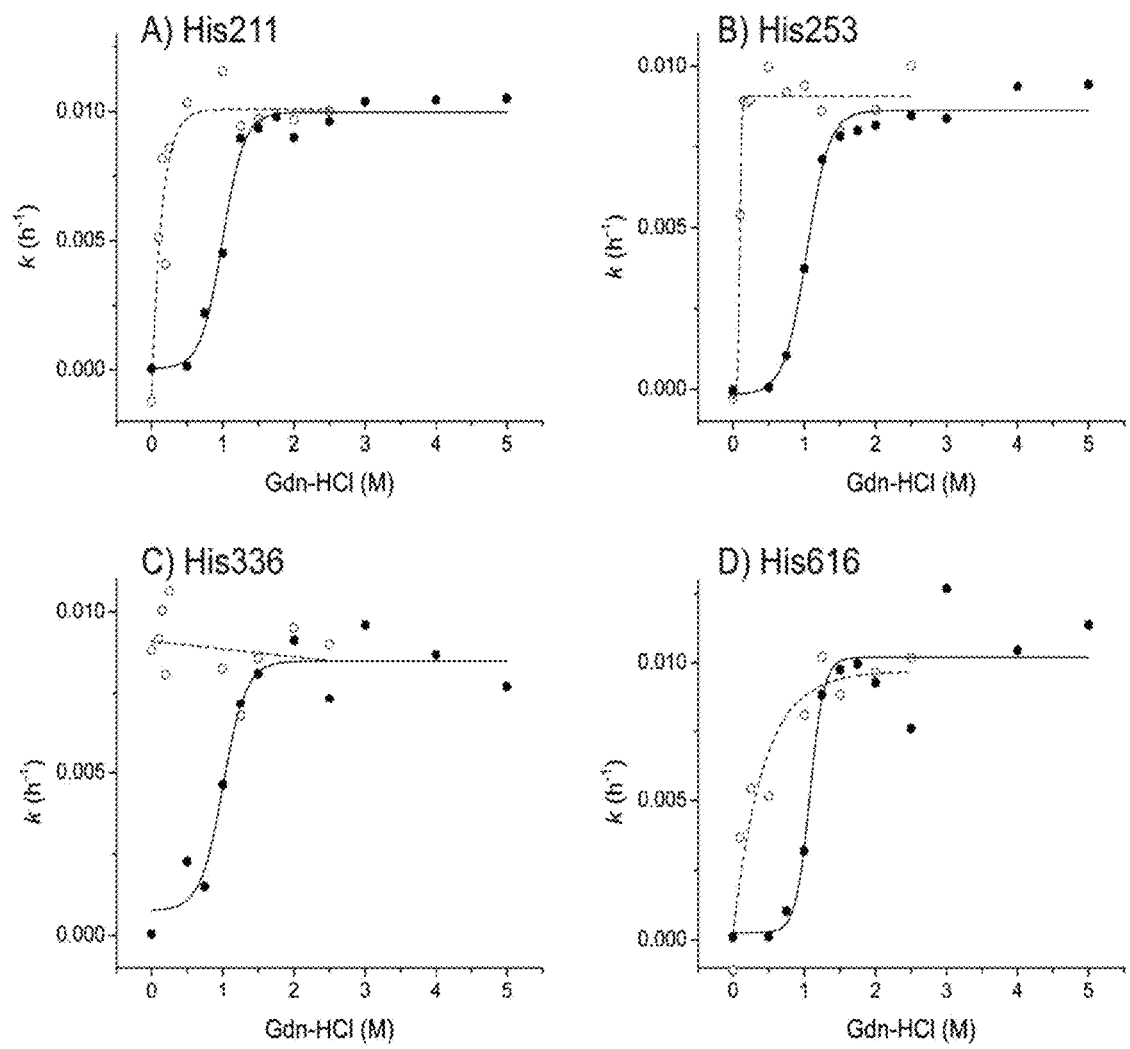
FIG. 9 shows graphs of Gdn-HCl denaturation curves of PA alone (---) and PA complexed with CMG2 (—) for four histidine residues, His211 (A), His253 (B), His336 (C), and His616 (D).

In FIG. 9, Gdn-HCl-induced denaturation curves of PA alone (dashed line) and PA complexed with CMG2 (solid line) monitored at these four histidine residues are shown. PA and the PA-CMG2 complex were incubated in 100 mM HEPES (pH* 7.5) at 37° C. for 48 h in various concentrations of Gdn-HCl. After the incubation, the protein was digested and the resulting peptides were analyzed by LC-MS/MS. The HDX rates of four histidine residues, His211 (A), His253 (B), His336 (C), and His616 (D), were monitored to follow the Gdn-HCl-induced denaturation of PA. PA denatured rapidly at very low Gdn-HCl concentrations, which prevented determination of the $C_m$ value (midpoint of the Gdn-HCl-induced unfolding transition) for PA alone accurately. Nevertheless, we estimated the $C_m$ values by visual inspection, which were ≈0.2, ≈0.2, and ≈0.5 M for His211, His253, and His616, respectively (Table 3).

TABLE 3

Transition Midpoints and Stabilities for the Gdn-HCl-Induced Unfolding of PA and PA Complexed with CMG2

| | | PA | | PA-CMG2 | |
|---|---|---|---|---|---|
| Residue | domain | $C_m$ (M) | ΔG (kcal mol−1) | $C_m$ (M)[a] | ΔG (kcal mol−1) |
| His211 | 1 | ≈0.2 | — | 1.00 ± 0.04 | 5.17 |
| His253 | 1 | ≈0.2 | — | 1.03 ± 0.04 | 4.36 |
| His336 | 2 | — | — | 1.01 ± 0.08 | 4.37 |
| His616 | 4 | ≈0.5 | — | 1.08 ± 0.06 | 5.11 |

[a]The standard errors are associated with the sigmoidal curve fitting.

The $C_m$ value at His336 could not be determined, because this histidine is already exposed well to solvent in the native structure as indicated by the high HDX rate for this residue at 0 M Gdn-HCl (FIG. 9C, dashed line). The $C_m$ values for PA complexed with CMG2 were ~2-5-fold larger than those for PA alone (approximately 1 M at all four histidine residues) as shown in Table 3. The data in FIG. 9 are representative of three separate experiments. The values of $C_m$ (molar) for the PA-CMG2 complex were reproducible to ±12%. His211 is ~70 Å from the binding interface. Thus, our data indicate that PA is stabilized throughout most of the protein by receptor binding, and the unfolding of these residues, despite being located in different domains, occurs at concomitant Gdn-HCl concentrations. In addition to the $C_m$ values, we were able to estimate the standard state Gibbs free energy values from linear extrapolation of the His-HDX values as a function of denaturant, in the presence of CMG2. The calculated $\Delta G°$ values were approximately 4-5 kcal mol−1 at all four histidine residues (Table 3), suggesting that all are stabilized to a similar extent.

Figure 10:
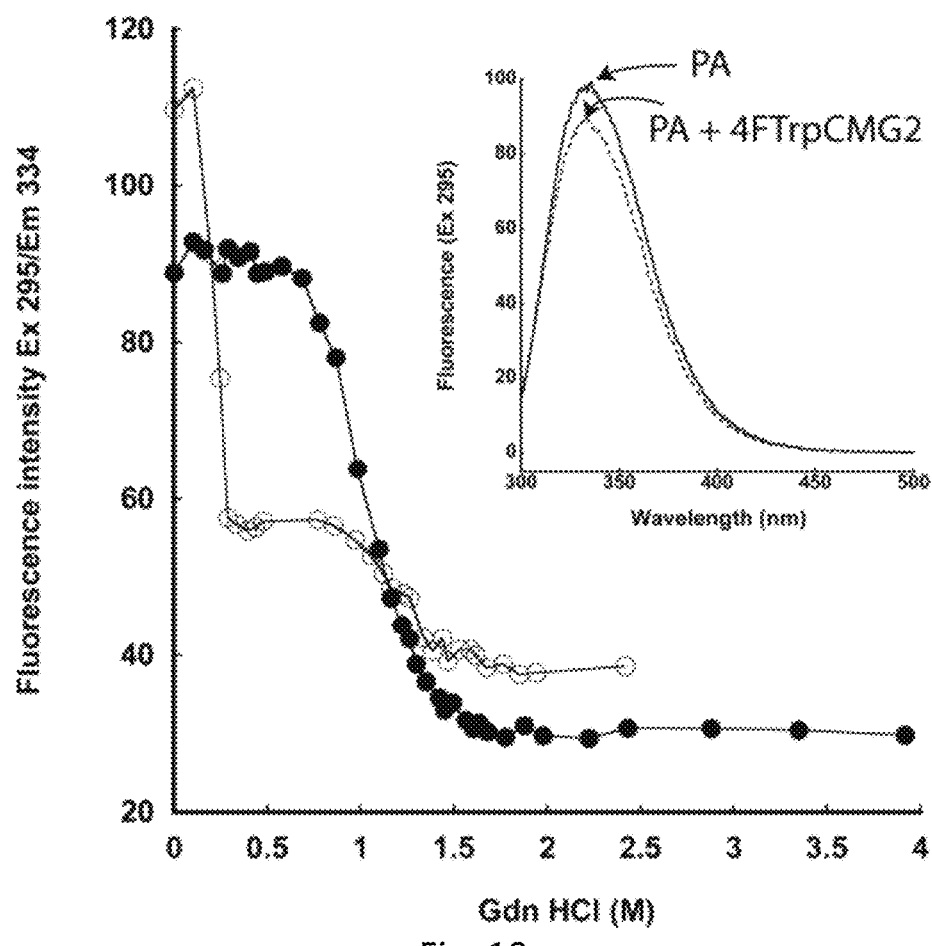
FIG. 10 shows a graph of the Gdn-HCl denaturation curves of PA alone (○) and PA complexed with CMG2 (•). The inset shows fluorescence emission spectra of PA and PA complexed with 4-FTrpCMG2.

Previous fluorescence and $^{19}F$ NMR unfolding experiments in urea have shown that PA unfolds in two transitions, the first transition being assigned to the unfolding of domains 1'-4 and the second transition being mainly due to the $PA_{20}$ domain, which after cleavage with furin can freely dissociate and is stable on its own. Here, we followed the Gdn-HCl-induced unfolding of PA by fluorescence in the presence of CMG2, where we have labeled CMG2 with 4-fluorotryptophan (4-FTrp). This effectively eliminates the fluorescence contribution from the sole tryptophan (Trp59) of CMG2, because 4-FTrp is a nonfluorescent analogue of tryptophan (see the inset of FIG. 10). FIG. 10 shows the Gdn-HCl denaturation curves of PA alone (o) and PA complexed with CMG2 (•). The fluorescence emission spectra of PA alone and PA complexed with 4-FTrpCMG2 in 100 mM HEPES (pH 7.5) containing 1 mM MgCl2 and various concentrations of Gdn-HCl were recorded by exciting the tryptophan residues in PA at 295 nm and monitoring the emitted light at 334 nm. The inset shows fluorescence emission spectra of PA and PA complexed with 4-FTrp-CMG2. The structure of CMG2 is largely unchanged upon labeling, as evidenced by the far-UV CD spectrum of wild-type (WT) CMG2 and 4-FTrpCMG2. Gdn-HCl-induced denaturation curves of PA alone and PA complexed with 4-FTrpCMG2 are shown in FIG. 10. As we observed previously in urea, PA undergoes two transitions by fluorescence, which we again have assigned to the unfolding of domains 1'-4 constituting the $PA_{63}$ region of PA at a low Gdn-HCl concentration (~0.2 M) and to the $PA_{20}$ domain at higher (~1.3 M) Gdn-HCl concentrations. In the presence of CMG2, we observed one single transition at a $C_m$ of ~1.3 M, suggesting that domains 1'-4 were significantly stabilized by receptor binding. We did not see a further increase in stability above that of the $PA_{20}$ domain, suggesting that receptor binding largely stabilizes residues up to the $PA_{20}$ region. In any case, these results agree well with the results obtained with the His-HDX-MS method.

Protease Susceptibility of PA and PA Bound to CMG2

Figure 11:
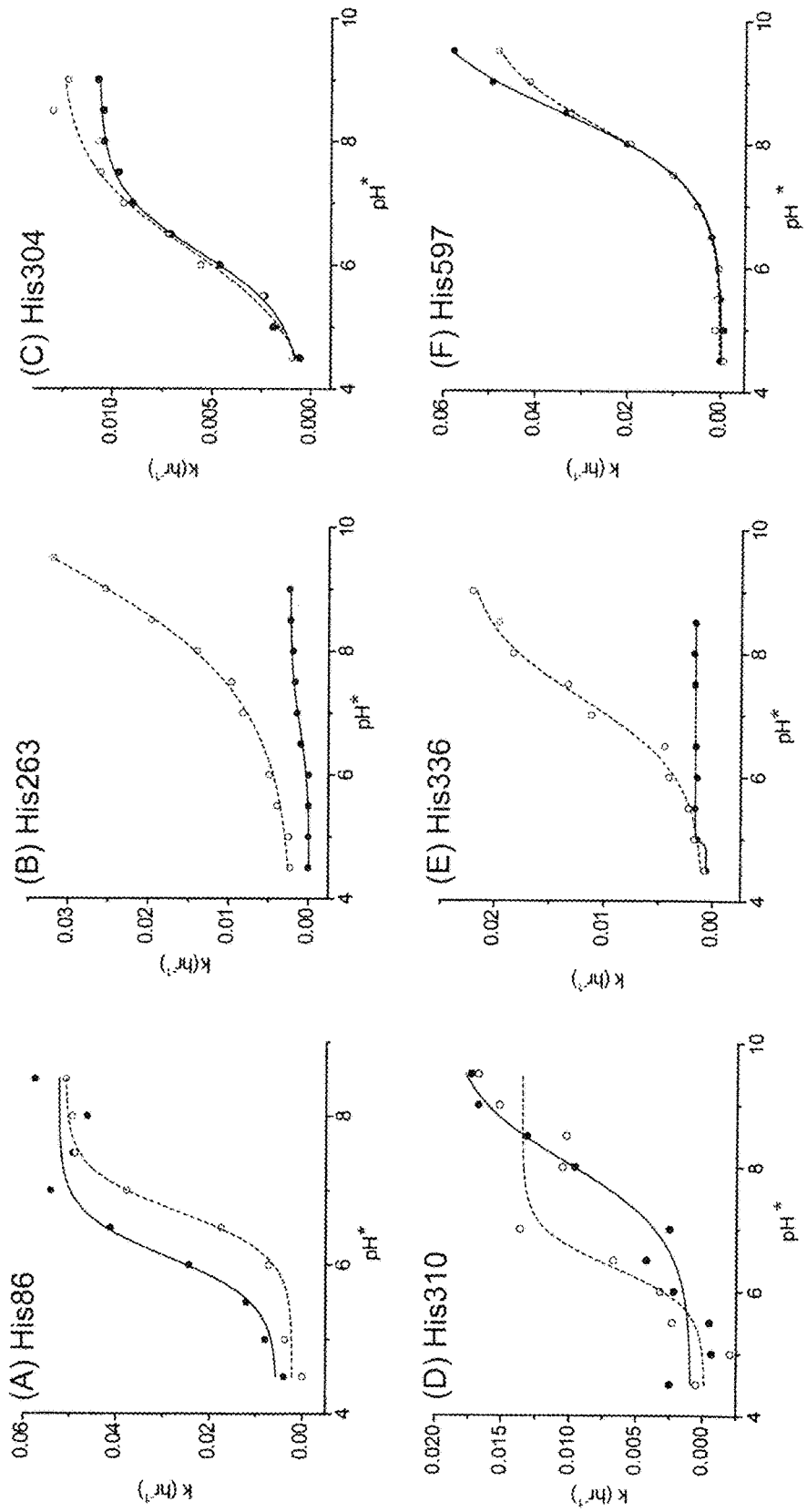
FIG. 11 shows a sulfate polyacrylamide gel electrophoresis (SDS-PAGE) image of Proteolysis of PA alone (A) and PA complexed with CMG2 (B) by thermolysin.

Resistance to proteolysis is an effective way to probe accessibility to unfolded conformations in a protein, and we hypothesized that CMG2 binding would "tighten" the structure of the protein and decrease the rate of proteolytic degradation. To test whether binding of CMG2 stabilizes PA against proteolysis, we incubated PA and the PA-CMG2 complex (1:2 ratio) at room temperature with 100 μg thermolysin for different periods of time (up to 120 min) and analyzed the resulting reactions by SDS-PAGE. Aliquots were withdrawn at the different time points and run on a 15% SDS-PAGE gel. In the case of PA alone, the undigested PA band disappeared within 30 s and appeared to be cleaved into two fragments (50 and 40 kDa) (FIG. 11A). The two fragments, however, did not last long, fading away within 60 min. In the case of PA complexed with CMG2, the undigested band similarly disappeared within 30 s; however, the generated 50 kDa band was clearly seen even after incubation for 120 min (FIG. 11B). The 40 kDa band faded away also within 60 min. To determine the thermolysin cleavage site, we analyzed the PA-CMG2 complex treated with thermolysin by LC-MS. We observed one major peak, in addition to the peaks that correspond to thermolysin and CMG2. The major peak gave a mass of 47007.4 Da and likely encompasses the 50 kDa band. The molecular weight matched well to the calculated molecular weight of the C-terminal portion of PA, Ile326-Gly745 (47002.5 Da). Thus, the 50 kDa band is likely the C-terminal portion of PA produced by the hydrolysis between Asp315 and Ile316. The site has a preferred sequence recognized by this protease (X-Ile, X-Leu, X-Val, or X-Phe, where X is any amino acid) and falls within the flexible region (His304-Ser319) that cannot be observed in the crystal structures of PA or the PA-CMG2 complex. The thermolysin resistance of the C-terminal fragment suggests that CMG2 remains bound to the C-terminal fragment after the proteolytic cleavage, thus providing continued resistance against thermolysin.

$pK_a$ Values and His-HDX Rates

In previous studies, we compared, using His-HDX-MS, the effect of CMG2 binding on the rate of exchange at pH* 9.5; however, we were unable to determine the $pK_a$ values of the histidines, which this technique also allows. Therefore, in a manner similar to our previous work, we conducted a pH* titration study on PA alone and the PA-CMG2 complex using His-HDX-MS. The protein was deuterated in different pH* buffers (4.5-9.0), digested, and then analyzed by LC-MS/MS. All 10 histidine residues were detected in different peptides, described in the supplementary information from Mullangi et al. (2014) Long-Range Stabilization of Anthrax Protective Antigen upon Binding to CMG2, Biochemistry, 53 (38), pp 6084-6091, incorporated by reference herein in its entirety. The rate constants (k) for HDX of those histidine residues were calculated directly from their precursor ion spectra. The obtained k values as a function of pH* for six histidine residues (His86, His263, His304, His310, His336, and His597) are shown in FIG. 12. We could not obtain interpretable sigmoid curves for His211, His253, His299, and His616 because of their slow HDX rates. PA and the PA-CMG2 complex were incubated at different pH* values (4.5-9.0) at 37° C. for 50 h. After the incubation, the protein was digested and the resulting peptides were analyzed by LC-MS/MS. The pH* dependencies of the k values for HDX for (A) His86, (B) His263, (C) His304, (D) His310, (E) His336, and (F) His597 are shown for PA alone (---) and PA complexed with CMG2 (—). All the histidine residues in FIG. 12 gave simple sigmoid curves corresponding to a single $pK_a$ except for His263 in PA, which showed a steep rise above pH* 7 without an explicit inflection point (FIG. 12B, dashed line).

We believe this curve reflects the increased local conformational fluctuation and reversible unfolding around this residue at alkaline pH*, causing the histidine residue to be exposed more to solvent, rather than reflecting the acid dissociation of this residue. The phenomenon was not observed for the same residue in the PA-CMG2 complex (FIG. 12B, solid line), suggesting that binding to the receptor increases the stability of this region against alkaline pH*.

The k value for His336 (FIG. 12E, solid line) in the PA-CMG2 complex was too low to produce interpretable sigmoidal curves.

Measured $pK_a$ values from the sigmoid curves for His86, His304, His310, His336, and His597 are shown in Table 4.

TABLE 4

$pK_a$ and $t_{1/2}$ Values of Histidine Residues in PA and the PA-CMG2 Complex[a]

| residue | do-main | $pK_a$ PA | $pK_a$ PA-CMG2 | $t_{1/2}$ (day) PA | $t_{1/2}$ (day) PA-CMG2 |
|---|---|---|---|---|---|
| His86  | 1 | 6.71 ± 0.04 | 6.10 ± 0.12 | 0.57 ± 0.01 | 0.55 ± 0.03 |
| His211 | 1 | ND[b] | ND[b] | 20.77[c] | 24.11[c] |
| His253 | 1 | ND[b] | ND[b] | >50[c] | >50[c] |
| His263 | 2 | ND[b] | 6.77 ± 0.15 | 1.13[c] | 12.45 ± 0.85 |
| His299 | 2 | ND[b] | ND[b] | 7.17[c] | 7.95[c] |
| His304 | 2 | 6.26 ± 0.18 | 6.19 ± 0.06 | 2.26 ± 0.12 | 2.71 ± 0.07 |
| His310 | 2 | 6.38 ± 0.25 | 8.06 ± 0.29 | 2.14 ± 0.20 | 1.50 ± 0.02 |
| His336 | 2 | 7.25 ± 0.13 | ND[b] | 1.26 ± 0.09 | 13.98[c] |
| His597 | 4 | 8.28 ± 0.04 | 8.49 ± 0.04 | 0.55 ± 0.01 | 0.42 ± 0.01 |
| His616 | 4 | ND[b] | ND[b] | 33.48[c] | 33.79[c] |

[a]The standard errors are associated with the sigmoidal curve fitting.
[b]The $pK_a$ could not be determined mainly because of the slow HDX rate.
[c]Calculated from k at pH 9.0 instead of using $k_{max}$, because $k_{max}$ could not be obtained because of the lack of an interpretable sigmoidal curve.

Significant changes in $pK_a$ for His86 and His310 were observed, which was surprising given that His86 is >90 Å from the binding interface. In general, the $pK_a$ of histidines depends on several factors; however, the lower the $pK_a$ (<6), the stronger the tendency to be buried and uncharged at neutral pH, while a higher $pK_a$ (>7.5) generally reflects the greater potential for charge-charge interactions. The $pK_a$ of His86 decreased 0.61 pH unit upon binding to CMG2 (from ~6.7 to 6.1), while the $pK_a$ of His310 increased 1.68 pH units. In previous work, we compared the distances of the histidine residues to potential hydrogen bond donors and/or acceptors and in general found that the distances became shorter in the presence of CMG2. Indeed, for His86, the distance to the Gln121 backbone carbonyl decreases from 3.43 to 3.07 Å, and this decreased distance is likely reflected in a slight lowering of the $pK_a$. In contrast to that of His86, the $pK_a$ of His310 increased 1.68 pH units upon binding to CMG2, from 6.26 to 8.06. We are not able to offer an interpretation of the observed $pK_a$ change of this residue because His310 is not observed in the crystal structures of PA and the PA-CMG2 complex. However, the increased $pK_a$ suggests that one or more acidic side chains (e.g., Asp or Glu) may come close to His310 upon binding to CMG2. Indeed, Glu308, Glu302, and Asp315 are local candidates for interacting with His310.

In addition to His86 and His310, we were able to determine the $pK_a$ values of His263 (for only the PA-CMG2 complex), His304, His336 (for only PA), and His597. The $pK_a$ of His263 in the PA-CMG2 complex was determined to be 6.77, which is close to the intrinsic $pK_a$ value of a histidine residue ($pK_a$≈6.5), suggesting little electrostatic influence of the neighboring groups on this residue. The $pK_a$ of His336 in PA was slightly higher (7.25) than the intrinsic $pK_a$ value of the histidine residue, suggesting there is a moderate influence of the electron-donating group(s) around this residue. The $pK_a$ values of His597 in both PA and the PA-CMG2 complex were shifted almost 2 pH units toward alkaline values (≥8), indicating there is a negatively charged group(s) in the proximity of this histidine. As expected, the imidazole ring of His597 is in the proximity of the carboxyl group of Asp608 and likely forms a salt bridge to this residue, in agreement with the crystal structure.

We previously reported the half-lives [$t_{1/2}$ (days)] of the HDX reactions of histidine residues in PA. Those $t_{1/2}$ values were calculated from the HDX rates obtained at a single pH* (9.5). In this study, we calculated the $t_{1/2}$ values from the maximal rate constant ($k_{max}$) obtained from the plateau to the alkaline side of the sigmoid titration curve. The $t_{1/2}$ values calculated in this way are considered to be more accurate, because they are calculated from the $k_{max}$ values obtained from the pH* titration curves fit to multiple data points. The $t_{1/2}$ values for His86, His263 (for only the PA-CMG2 complex), His304, His310, His336 (for only PA), and His597 were successfully determined from their $k_{max}$ values and are listed in Table 4. We could not obtain interpretable sigmoidal curves for the remaining histidine residues mainly because of their slow HDX rates; therefore, the $t_{1/2}$ values for those histidine residues were calculated from the k obtained at pH* 9.0.

The significant increases in $t_{1/2}$ values due to receptor binding were observed for three histidine residues, His263, His304, and His336, suggesting that their solvent accessibilities decreased upon receptor binding. The increased $t_{1/2}$ value for His263 is probably due to the increased level of stabilization of the local structure against alkaline pH* that occurs upon receptor binding as discussed above. Because His263 and His336 are observed in structures of PA and the PA-CMG2 complex, we compared the solvent accessible surface area (ASA) values for the $C_2$ atoms of the histidine residues. The ASA values for His263 and His336 in both structures were comparable (His263, 15.5 Å2 for PA and 11.1 Å2 for the PA-CMG2 complex; His336, 20.3 Å2 for PA and 18.1 Å2 for the PA-CMG2 complex). Therefore, we cannot explain the results based on the ASA values. This discrepancy may reflect the difference in protein structures in the solution and crystals. The HDX reaction of the $C_2$ hydrogen of the imidazole group occurs only when the neutral and protonated forms of the imidazole group are in equilibrium and the $C_2$ atom is in direct contact with water. Therefore, the HDX reaction can be diminished when the number of water molecules assisting the acid-base equilibrium of the imidazole group or having contact with the $C_2$ atom is reduced. Thus, our results indicate that receptor binding tightens the structure of PA, which leads to expelling water molecules around these histidine residues.

Long-Range Stabilization of PA Upon CMG2 Binding

Our Gdn-HCl-induced unfolding experiments clearly show that PA is stabilized by CMG2, and the stabilization occurs not only in the domain that directly interacts with CMG2 (His616 located in domain 4) but also in domains that do not have direct contact with CMG2 (His211 and His253 located in domain 1'). Thus, we can safely say that both our combined His-HDX, fluorescence, and protease sensitivity assays indicate that the stabilization afforded by binding of CMG2 occurs up to His211 (which is ~70 Å from the binding interface) does not seemingly further influence the stability of the $PA_{20}$ domain. Nonetheless, our pH titration study using His-HDX-MS revealed that the microenvironment around histidine residues in $PA_{20}$, domain 2, and domain 4 changes upon receptor binding. The altered $pK_a$ of His86 in the $PA_{20}$ domain indicates that the binding to CMG2 influences the microenvironment of His86 even though the residue is far from the CMG2 binding interface (>90 Å).

Influence of Receptor Binding on Domain 2 and Domain 4 Dynamics

How does receptor binding influence residues that are far from the binding interface? Previous experiments have indicated that domain 2 and domain 4 are part of a hinge that dictates the oligomeric assembly of PA$_{63}$, such that a tighter interaction favors the formation of heptamers, whereas a weaker interaction may favor the formation of octamers. This implies that domain 2 and domain 4 are capable of hingelike dynamic motions that likely give rise to an overall plasticity in the protein. By anchoring the domain 2-domain 4 interface, hingelike motions are prevented, which in turn would effectively stabilize domain-domain interactions and other noncovalent interactions within the protein.

The PA-CMG2 Complex as a Potential Immunogen in an Anthrax Vaccine

PA is the key component of anthrax vaccines currently licensed as well as vaccines under development. Efforts to develop protective adjuvants that do not require the use of a cold chain for storage in areas where a cold chain is not accessible or feasible are ongoing. Our study finds that CMG2 thermodynamically stabilizes PA, and thus, CMG2 may prevent structural perturbations to the protein under long-term storage conditions. Further, the addition of CMG2 slowed the rate of proteolysis by thermolysin. Addition of CMG2 to the vaccine formulation may prevent premature degradation of the protein post-injection, possibly allowing for a greater proportion of PA to ultimately be presented on antigen-presenting cells. Finally, depletion of the actual PA concentration amenable for interacting with the host immune system likely occurs because of the interaction of PA with receptors present on the surface of host cells, and the inclusion of CMG2 in a vaccine formulation should prevent such a depletion of PA.

His-HDX-MS as a Tool To Investigate Protein Stability

Studies have shown that amide HDX in combination with mass spectrometry can be used to provide information about the stability of specific regions within a protein. This work demonstrates that His-HDX-MS is complementary to amide HDX, and to other conventional methods such as fluorescence spectroscopy and CD spectroscopy for monitoring protein stability. The advantages of this method over other methods include (1) the ability to follow the side chain stability at a single histidine, which may be more sensitive to the folded state of a protein (because it may be the last part to be stabilized), and to monitor the stabilities of different sites within a protein simultaneously, (2) compared to NMR or CD, the absence of a requirement for large amounts of protein, (3) the fact that proteins do not have to be pure, because mass spectrometry can detect peptide masses even in complex mixtures, and (4) the fact that proteins can be in seemingly any environment, such as a soluble monomer or part of a large oligomeric multiprotein complex within the membrane. These advantages will allow us to study the stabilities of proteins in more complex structures and cellular milieu.

We claim:

1. A method for inducing an immunogenic response in a subject against *B. anthracis*, said method comprising administering to the subject a therapeutically-effective amount of an immunogenic composition against *Bacillus anthracis*, said composition comprising a stabilized protective antigen complex, said complex comprising *Bacillus anthracis* protective antigen protein and capillary morphogenesis protein-2, wherein said capillary morphogenesis protein-2 is bound to said protective antigen protein along a binding interface.

2. The method of claim 1, wherein said binding interface comprises direct interaction of capillary morphogenesis protein-2 with His616 in domain 4 of the protective antigen protein.

3. The method of claim 1, wherein said protective antigen protein consists of four domains, wherein said protective antigen protein in said complex has decreased flexibility in an interface between domain 2 and domain 4 as compared to said protective antigen protein before complexation with said capillary morphogenesis protein-2.

4. The method of claim 1, wherein said protective antigen protein is a polypeptide that has at least 80% sequence identity to SEQ ID NO. 1.

5. The method of claim 1, wherein said protective antigen protein comprises a modified histidine residue with a fluorine at the 2-position so that the pKa of said modified histidine residue is less than about 3.

6. The method of claim 5, wherein at least 50% of the histidine residues are modified to have a pKa of less than about 3.

7. The method of claim 1, wherein the protective antigen protein comprises at least $PA_{20}$ of a wild type protective antigen protein.

8. The method of claim 7, wherein residue His86 of said $PA_{20}$ has an altered pKa.

9. The method of claim 1, wherein said capillary morphogenesis protein-2 comprises at least the von Willebrand factor A domain A of capillary morphogenesis protein-2.

10. The method of claim 1, wherein said capillary morphogenesis protein-2 has been synthesized in vitro.

11. The method of claim 1, wherein said protective antigen protein has a thermal stability that is about 20° C. higher than the thermal stability of uncomplexed protective antigen protein.

12. The method of claim 1, said composition comprising a therapeutically effective amount of said stabilized protective antigen complex dispersed in a pharmaceutically acceptable carrier.

13. The method of claim 1, said composition further comprising an antibody against lethal factor and/or an antibody against edema factor of *B. anthracis* dispersed in said carrier.

14. The method of claim 1, wherein said subject is suffering from *B. anthracis* infection before said administering.

15. The method of claim 1, wherein said subject is free of observable symptoms of *B. anthracis* infection before said administering.

16. The method of claim 1, wherein said subject is at risk of developing *B. anthracis* infection before said administering.

17. The method of claim 1, further comprising co-administering one or more of antibodies against lethal factor, antibodies against edema factor, antibodies against a second protective antigen, amoxicillin, penicillin G procaine, ciprofloxacin, doxycycline, chloramphenicol, clindamycin, tetracycline, rifampin, and/or vancomycin.

18. The method of claim 1, wherein said administering is selected from the group consisting of intramuscularly, subcutaneously, intradermally, intravenously, intranasally, and orally.

19. The method of claim 1, comprising administering a unit dosage form of said immunogenic composition to said subject.

* * * * *